(12) United States Patent
Kimsey et al.

(10) Patent No.: US 11,504,128 B2
(45) Date of Patent: Nov. 22, 2022

(54) SHAFT ATTACHMENT FEATURE FOR CIRCULAR SURGICAL STAPLER

(71) Applicant: Ethicon LLC, Guaynabo, PR (US)

(72) Inventors: John S. Kimsey, Walton, KY (US); Shane R. Adams, Lebanon, OH (US); Vijay K. Sakhare, Mason, OH (US)

(73) Assignee: Cilag GmbH International, Zug (CH)

(*) Notice: Subject to any disclaimer, the term of this patent is extended or adjusted under 35 U.S.C. 154(b) by 0 days.

(21) Appl. No.: 16/887,182

(22) Filed: May 29, 2020

(65) Prior Publication Data

US 2021/0369279 A1 Dec. 2, 2021

(51) Int. Cl.
*A61B 17/068* (2006.01)
*A61B 17/115* (2006.01)
*A61B 17/00* (2006.01)

(52) U.S. Cl.
CPC . *A61B 17/1155* (2013.01); *A61B 2017/00407* (2013.01); *A61B 2017/00477* (2013.01); *A61B 2017/00986* (2013.01)

(58) Field of Classification Search
CPC .......................... A61B 17/068; A61B 17/1155
See application file for complete search history.

(56) References Cited

U.S. PATENT DOCUMENTS

| | | | | |
|---|---|---|---|---|
| 3,552,626 A | * | 1/1971 | Astafiev | A61B 17/1155 227/76 |
| 4,304,236 A | * | 12/1981 | Conta | A61B 17/115 227/179.1 |
| 4,573,468 A | * | 3/1986 | Conta | A61B 17/115 227/179.1 |
| 5,047,039 A | * | 9/1991 | Avant | A61B 17/11 606/148 |
| 5,139,513 A | * | 8/1992 | Segato | A61B 17/115 227/179.1 |
| 5,205,459 A | * | 4/1993 | Brinkerhoff | A61B 17/115 227/179.1 |
| 5,271,544 A | | 12/1993 | Fox et al. | |
| 5,275,322 A | | 1/1994 | Brinkerhoff et al. | |

(Continued)

FOREIGN PATENT DOCUMENTS

WO    WO 2015/065484 A1    5/2015

OTHER PUBLICATIONS

U.S. Appl. No. 16/887,140 entitled, "Knife for Circular Surgical Stapler," filed May 29, 2020.

(Continued)

*Primary Examiner* — Eyamindae C Jallow
(74) *Attorney, Agent, or Firm* — Frost Brown Todd LLC

(57) ABSTRACT

An apparatus includes a body, a shaft, and a stapling head assembly. The shaft extends distally from the body and includes a coupling feature. The coupling feature includes threading or at least one barb. The stapling head assembly is configured to cut and staple tissue. The stapling head assembly is positioned at a distal end of the shaft. The stapling head assembly includes a knife member and a body member. The knife member includes a circular cutting edge configured to cut through tissue. The body member is configured to house the knife member. The body member includes a coupling feature that is configured to mechanically couple with the coupling feature of the shaft. The coupling feature of the body member includes threading or at least one barb.

20 Claims, 27 Drawing Sheets

(56) References Cited

U.S. PATENT DOCUMENTS

| | | | |
|---|---|---|---|
| 5,285,945 A | 2/1994 | Brinkerhoff et al. | |
| 5,292,053 A | 3/1994 | Bilotti et al. | |
| 5,333,773 A | 8/1994 | Main et al. | |
| 5,350,104 A | 9/1994 | Main et al. | |
| 5,533,661 A | 7/1996 | Main et al. | |
| 6,068,636 A * | 5/2000 | Chen | A61B 17/1114 606/153 |
| 7,918,377 B2 | 4/2011 | Measamer et al. | |
| 8,910,847 B2 * | 12/2014 | Nalagatla | H04B 7/0682 227/179.1 |
| 9,161,803 B2 | 10/2015 | Yates et al. | |
| 9,713,469 B2 | 7/2017 | Leimbach et al. | |
| 9,907,552 B2 | 3/2018 | Measamer et al. | |
| 9,936,949 B2 | 4/2018 | Measamer et al. | |
| 10,092,292 B2 | 10/2018 | Boudreaux et al. | |
| 10,226,253 B2 | 3/2019 | DiNardo et al. | |
| 10,478,189 B2 | 11/2019 | Bear et al. | |
| 2012/0061448 A1 * | 3/2012 | Zingman | A61B 17/1155 227/175.2 |
| 2014/0144968 A1 * | 5/2014 | Shelton, IV | A61B 17/0644 227/175.1 |
| 2015/0083772 A1 | 3/2015 | Miller et al. | |
| 2015/0320420 A1 | 11/2015 | Penna et al. | |
| 2017/0258471 A1 * | 9/2017 | DiNardo | A61B 17/1155 |
| 2018/0132849 A1 | 5/2018 | Miller et al. | |
| 2018/0132853 A1 | 5/2018 | Miller et al. | |
| 2018/0310938 A1 | 11/2018 | Kluener et al. | |
| 2019/0216462 A1 | 7/2019 | Milliman | |
| 2020/0281596 A1 | 9/2020 | Wise et al. | |

OTHER PUBLICATIONS

International Search Report and Written Opinion dated Sep. 21, 2021, for International Application No. PCT/EP2021/064397, 22 pages.

* cited by examiner ns of a shaft assembly
SHAFT ATTACHMENT FEATURE FOR CIRCULAR SURGICAL STAPLER

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis, an end-to-side anastomosis, or a side-to-side anastomosis. The anastomosis may provide a substantially unobstructed flow path from one portion of the digestive tract to the other portion of the digestive tract, without also providing any kind of leaking at the site of the anastomosis.

One example of an instrument that may be used to provide an anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910, 847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; and U.S. Pat. No. 9,713,469, entitled "Surgical Stapler with Rotary Cam Drive," issued Jul. 25, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
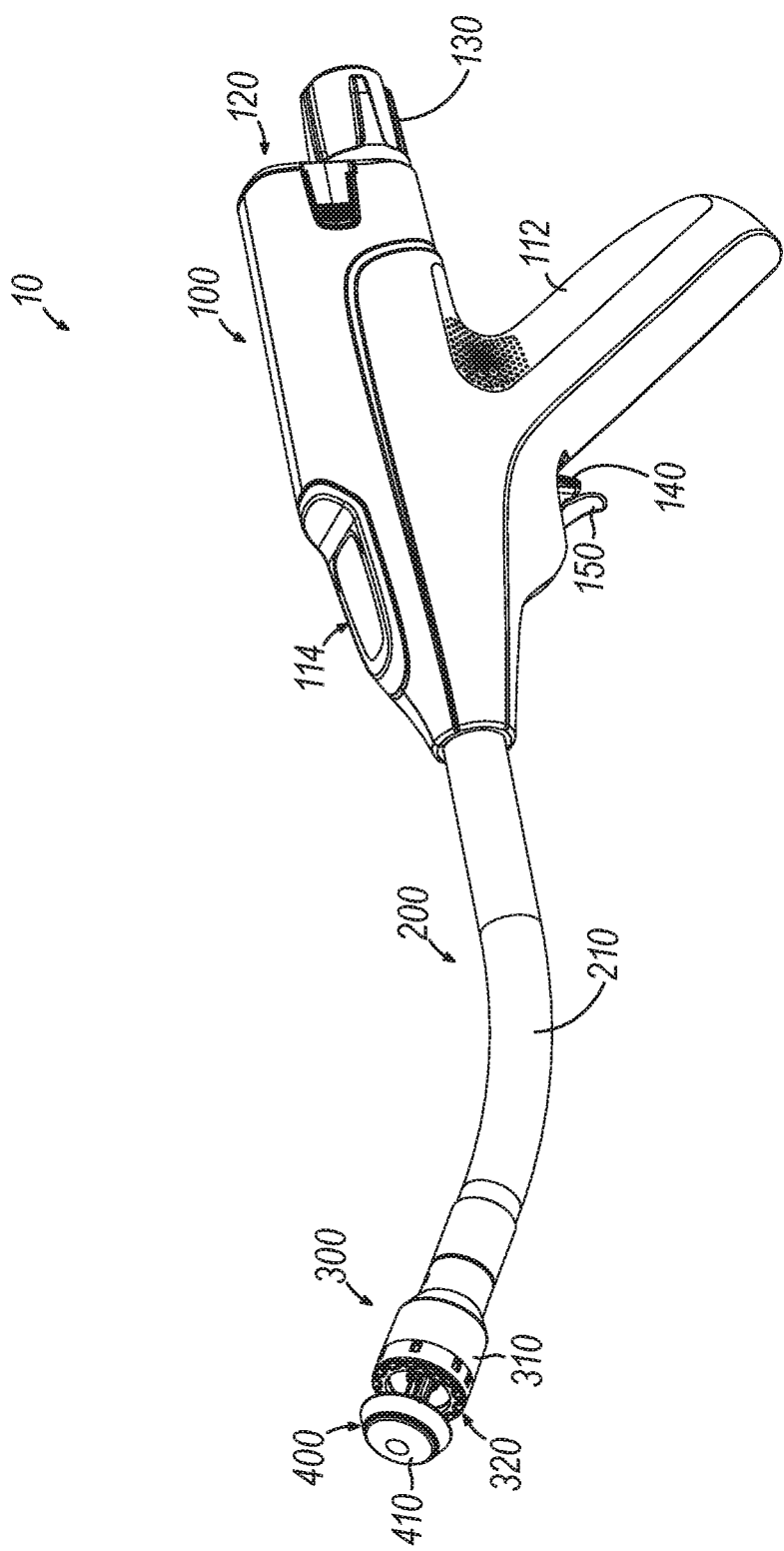
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

This application incorporates by reference the disclosures of U.S. Pub. No. 2015/0083772, entitled "Surgical Stapler with Rotary Cam Drive and Return," published on Mar. 26, 2015, now abandoned; U.S. Pat. No. 9,907,552, entitled "Control Features for Motorized Surgical Stapling Instrument," issued on Mar. 6, 2018; U.S. Pat. No. 10,478,189, entitled "Method of Applying an Annular Array of Staples to Tissue," issued on Nov. 19, 2019; U.S. Pub. No. 2018/0132853, entitled "Circular Stapler with Recessed Deck," published May 17, 2018; issued as U.S. Pat. No. 10,980,542 on Apr. 20, 2021; U.S. Pub. No. 2018/0132849, entitled "Staple Forming Pocket Configurations for Circular Surgical Stapler Anvil," published May 17, 2018, now abandoned; U.S. Pub. No. 2018/0310938, entitled "Hysteresis Removal Feature in Surgical Stapling Instrument," published Nov. 1, 2018, issued as U.S. Pat. No. 10,695,068 on Jun. 30, 2020.

I. Overview of Exemplary Circular Stapling Surgical Instrument

Figure 2:
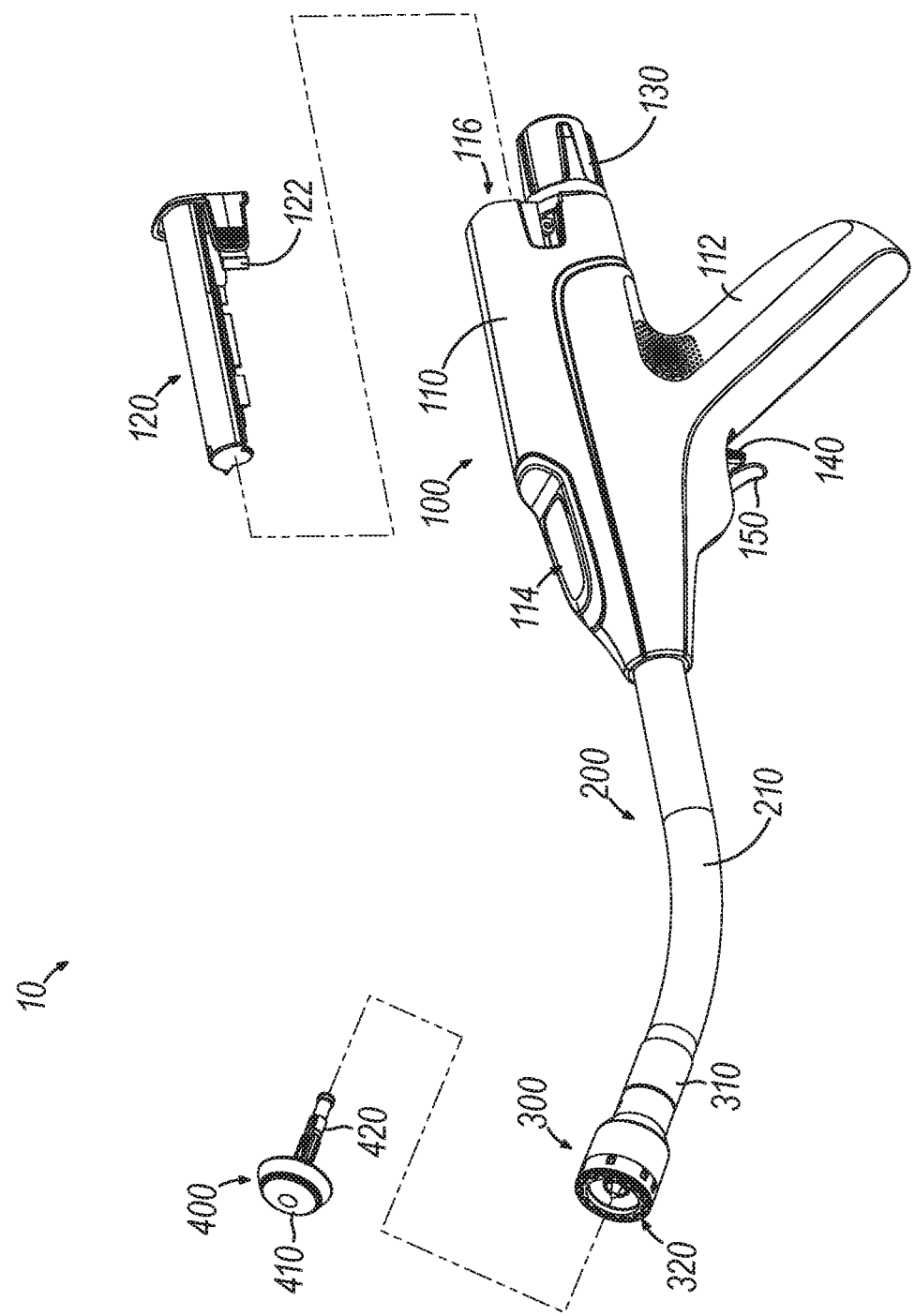
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end, side-to-side, or end-to-side anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (100) further includes a user feedback feature (114). In some versions, a series of hash marks, colored regions, and/or other fixed indicators are positioned adjacent to user feedback feature (114). Various suitable alternative features and configurations for handle assembly (100) will be apparent to those of ordinary skill in the art in view of the teachings herein.

Instrument (10) of the present example further includes a battery pack (120). Battery pack (120) is operable to provide electrical power to a motor (not shown) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery pack (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (200) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

II. Exemplary Drive Assembly

Figure 3:
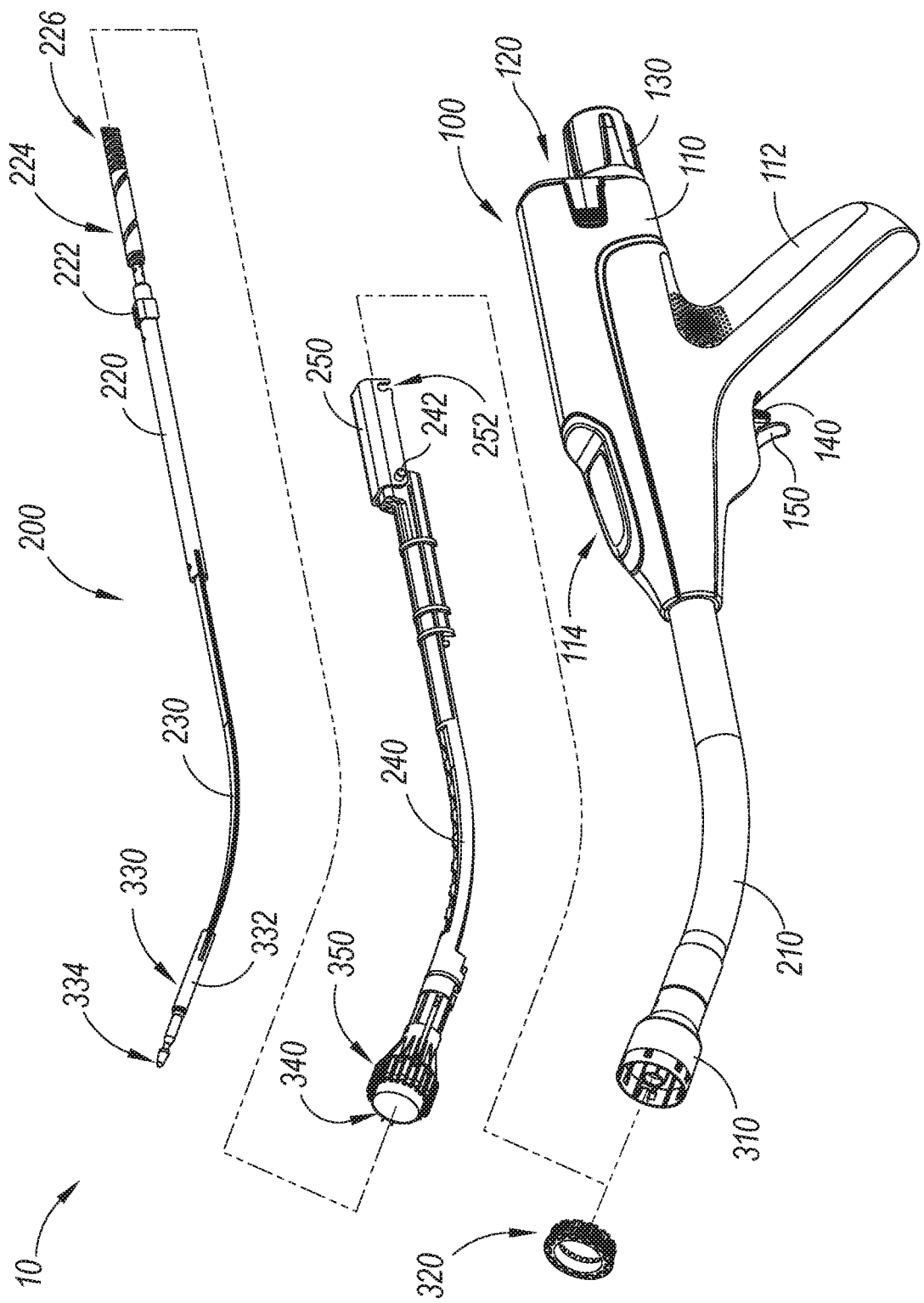
FIG. 3 depicts an exploded perspective view of the circular stapler of FIG. 1, with portions of a shaft assembly shown separately from each other.

FIG. 3 shows various components of shaft assembly (200), which couples components of stapling head assembly (300) with components of handle assembly (100). In particular, and as noted above, shaft assembly (200) includes an outer sheath (210) that extends between handle assembly (100) and a body member (310) (also referred to as a "casing"). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of a shaft (332) of a trocar (330). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to shaft (332) of trocar (330). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226).

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Drive bracket (250) includes notches (252).

While not shown in FIG. 3, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

As shown in FIG. 3, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, firing trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

III. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 4:
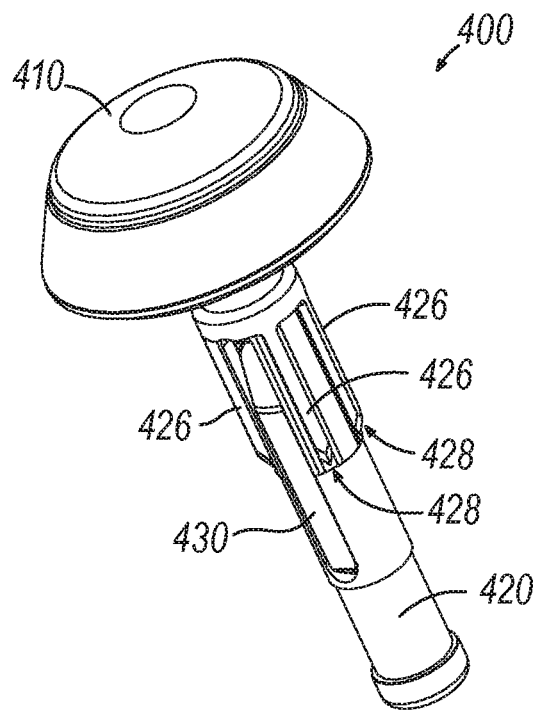
FIG. 4 depicts a perspective view of the anvil of the circular stapler of FIG. 1.
Figure 5:
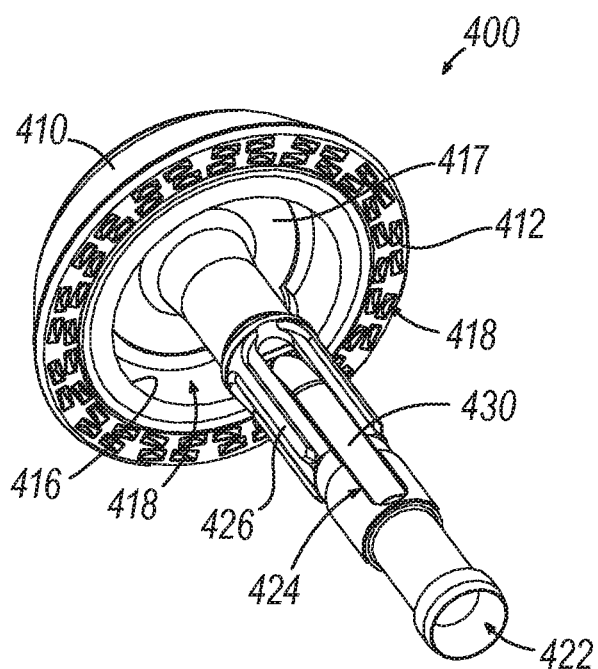
FIG. 5 depicts another perspective view of the anvil of FIG. 4.
Figure 6:
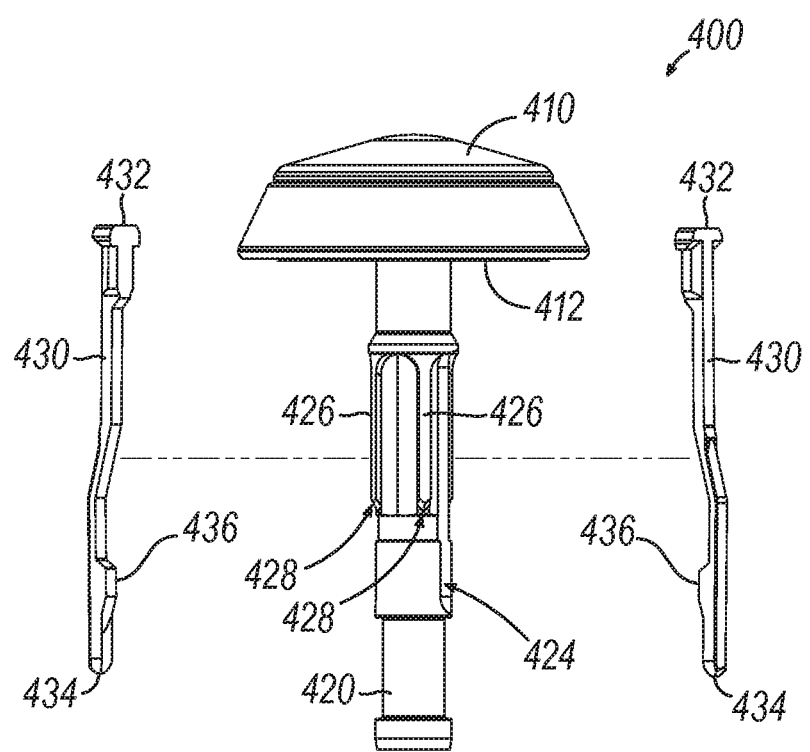
FIG. 6 depicts an exploded side elevational view of the anvil of FIG. 4.

As best seen in FIGS. 4-6, anvil (400) of the present example comprises a head (410) and a shank (420). Head (410) includes a proximal surface (412) that defines a plurality of staple forming pockets (414). Staple forming pockets (414) are arranged in two concentric annular arrays in the present example. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 4, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that proximal ends (434) are positioned at the proximal ends of lateral openings (424), which are formed through the sidewall of shank (420). Lateral openings (424) thus provide clearance for proximal ends (434) and latch shelves (436) to deflect radially outwardly from the longitudinal axis defined by shank (420). However, latch members (430) are configured to resiliently bias proximal ends (434) and latch shelves (436) to pivot radially inwardly toward the longitudinal axis defined by shank (420). Latch members (430) thus act as retaining clips. This allows anvil (400) to be removably secured to trocar (330) of stapling head assembly (300) as will be described in greater detail below. It should be understood, however, that latch shelves (436) are merely optional. Anvil (400) may be removably secured to trocar (330) using any other suitable components, features, or techniques.

As best seen in FIGS. 4-5, shank (420) of the present example includes a set of longitudinally extending splines (426) that are spaced about shank (420) in an angular array. The proximal end of each spline (426) includes a respective lead-in edge (428). A plurality of longitudinally extending splines (316) (see FIG. 8) are equidistantly spaced in an angular array within bore (314). As described in greater detail below, splines (426) are configured to engage corresponding splines (316) of body member (310) of stapling head assembly (300) in order to consistently provide a predetermined angular alignment between anvil (400) and stapling head assembly (300). As also described below, this angular alignment may ensure that staple forming pockets (414) of anvil (400) are consistently angularly aligned appropriately with staple openings (324) of stapling head assembly (300).

In some instances, it may be desirable to change the configuration and arrangement of staple forming pockets (414) in anvil (400). It should be understood that reconfiguring and rearranging staple forming pockets (414) may result in reconfiguration and rearrangement of staples (90) that are formed by staple forming pockets (414). For instance, the configuration and arrangement of staple forming pockets (414) may affect the structural integrity of an anastomosis (70) that is secured by staples (90). In addition, the configuration and arrangement of staple forming pockets (414) may affect the hemostasis that is achieved at an anastomosis (70) that is secured by staples (90). The following description relates to several exemplary variations of anvil (400), providing staple forming pocket configurations and arrangements that differ from those of staple forming pockets (414). Various suitable ways in which the alternatives to anvil (400) described below may be incorporated into instrument (10) will be apparent to those of ordinary skill in the art in view of the teachings herein.

For example, the staples formed using an exemplary alternative anvil may have an appearance similar to at least some of the staples shown and described in U.S. Pat. No. 10,092,292, entitled "Staple Forming Features for Surgical Stapling Instrument," issued Oct. 9, 2018, the disclosure of which is incorporated by reference herein. By way of further example only, the staples formed may have an appearance similar to at least some of the staples shown and described in U.S. Pub. No. 2018/0132849, entitled "Staple Forming Pocket Configurations for Circular Surgical Stapler Anvil," published May 17, 2018, now abandoned, the disclosure of which is incorporated by reference herein.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

IV. Exemplary Stapling Head Assembly

A. Overview

Figure 7:
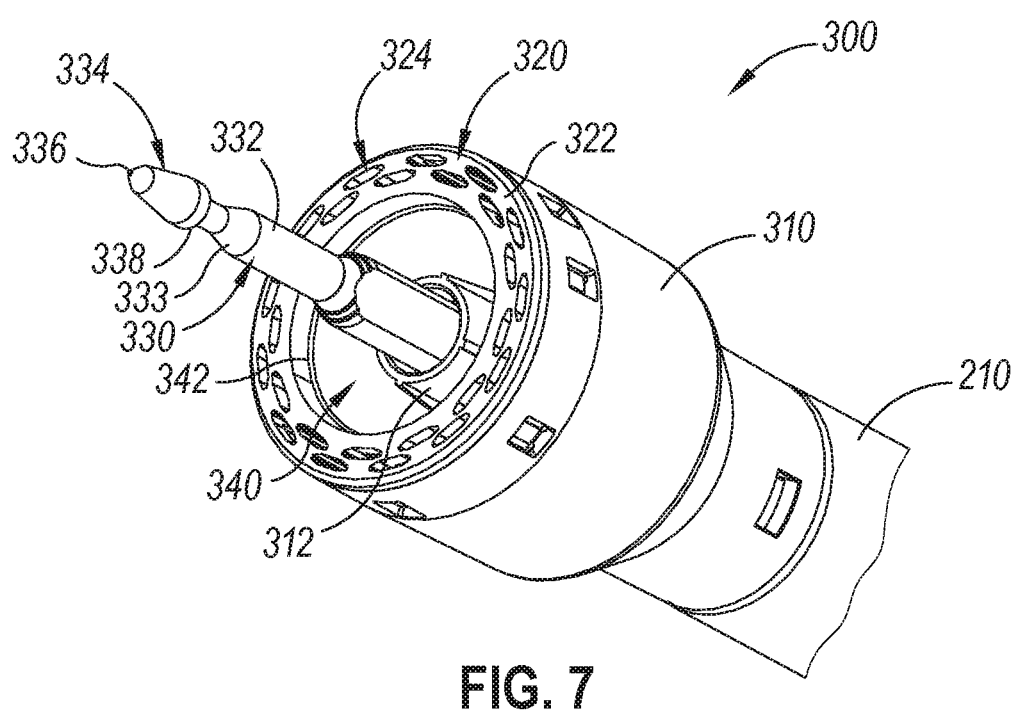
FIG. 7 depicts a perspective view of a stapling head assembly coupled with a shaft assembly of the circular stapler of FIG. 1.
Figure 8:
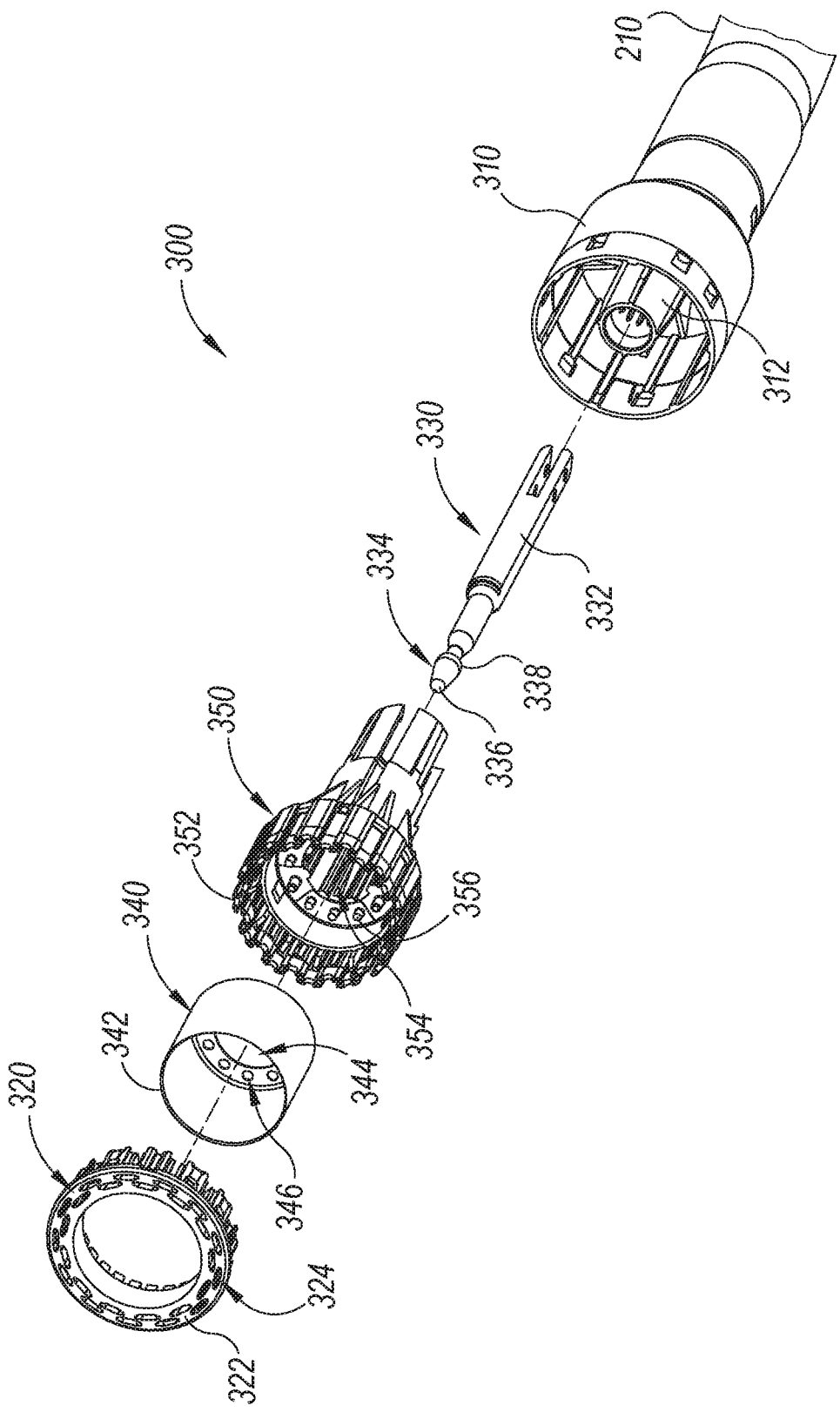
FIG. 8 depicts an exploded perspective view of the stapling head assembly coupled with the shaft assembly of FIG. 7.

As best seen in FIGS. 7-8, stapling head assembly (300) of the present example is coupled to a distal end of shaft assembly (200) and comprises body member (310) and a slidable staple driver member (350). Body member (310) includes a distally extending cylindraceous inner core member (312). Body member (310) is fixedly secured to an outer sheath (210) of shaft assembly (200). Body member (310) and outer sheath (210) thus serve together as a mechanical ground for stapling head assembly (300).

As shown in FIG. 8, inner core member (312) of body member (310) defines a bore (314). When shank (420) is secured to trocar (330) and trocar (330) is retracted proximally, the inner diameter of bore (314) of inner core member (312) of body member (310) laterally constrains latch members (430) to maintain engagement between latch shelves (436) and proximal surface (338) of a head (334) of trocar (330). This engagement prevents anvil (400) from being released from trocar (330) during firing of stapling head assembly (300). The distal ends of splines (316) include lead-in edges (318) that are configured to complement lead-in edges (428) of splines (426) on shank (420) of anvil (400). In particular, after shank (420) is secured to trocar (330) as described in greater detail below, and as anvil (400) is thereafter retracted proximally relative to stapling head assembly (300) as also described in greater detail below, lead-in edges (318, 428) may cooperatively engage each other to drive anvil (400) to rotate relative to trocar (330) to angularly align splines (426) of anvil (400) with the gaps between splines (316) of body member (310). Thus, splines (316, 426) are configured to cooperate with each other to ensure that staples ejected through staple openings (324) are accurately driven into corresponding staple forming pockets (414) on a consistent basis, regardless of the angular orientation of anvil (400) relative to stapling head assembly (300) at the time anvil (400) is initially secured to trocar (330).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and head (334). Head (334) includes a pointed tip (336) and an inwardly extending proximal surface (338). Shaft (332) thus provides a reduced outer diameter just proximal to head (334), with proximal surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within body member (310) in response to activation of the motor as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive inner core member (312) of body member (310). An annular array of studs (356) project distally from a distally presented surface surrounding bore (354).

A knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) defines an opening (344) that is configured to coaxially receive an inner core member (e.g., inner core member (312) of body member (310)). Knife member (340) includes an annular array of openings (346). Annular array of openings (346) formed in knife member (340) is configured to complement the annular array of studs (356) of staple driver member (350), such that knife member (340) is fixedly secured to staple driver member (350) via studs (356) and openings (346). By way of example only, studs (356) may be heat staked to knife member (340) using techniques known in the art. Other suitable structural relationships between knife member (340) and staple driver member (350) will be apparent to those of ordinary skill in the art in view of the teachings herein.

A deck member (320) is fixedly secured to body member (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should also be understood that, in some instances, the configuration and arrangement of staple openings (324) in deck member (320) may be modified just like the arrangement of staple forming pockets (414). It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein. As best seen in FIG. 7, deck member (320) defines an inner diameter that is just slightly larger than the outer diameter defined by knife member (340). Deck member (320) is thus configured to allow knife member (340) to translate distally to a point where cutting edge (342) is distal to deck surface (322).

B. Couplings Between Shaft Assembly and Stabling Head Assembly

Figure 9:
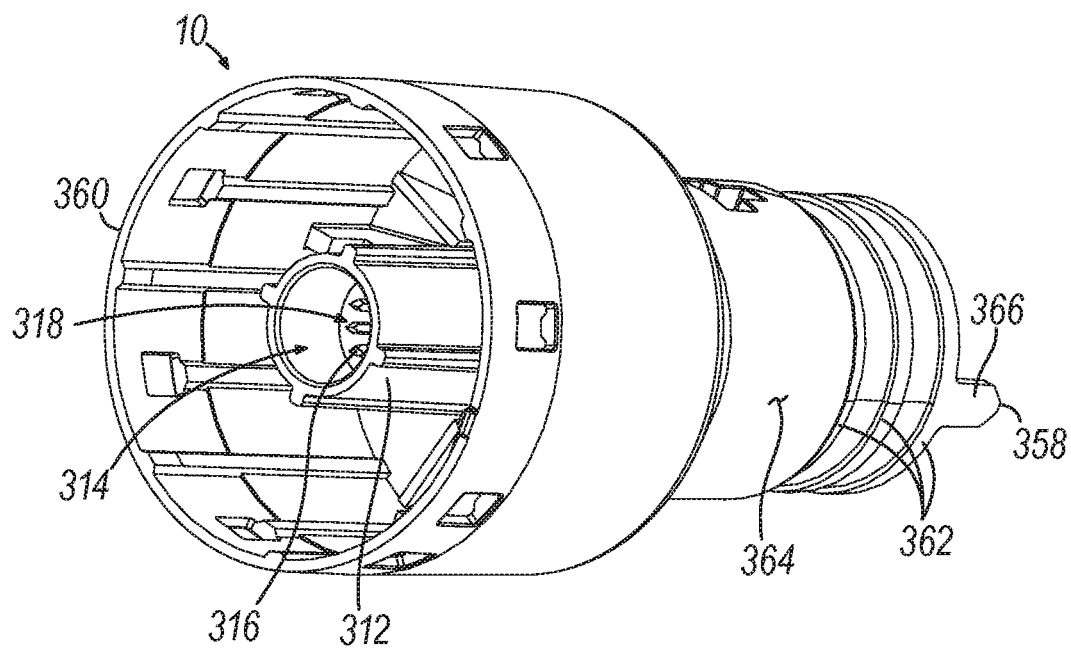
FIG. 9 depicts a perspective view of a body member of the stapling head assembly of FIG. 8.
Figure 10:
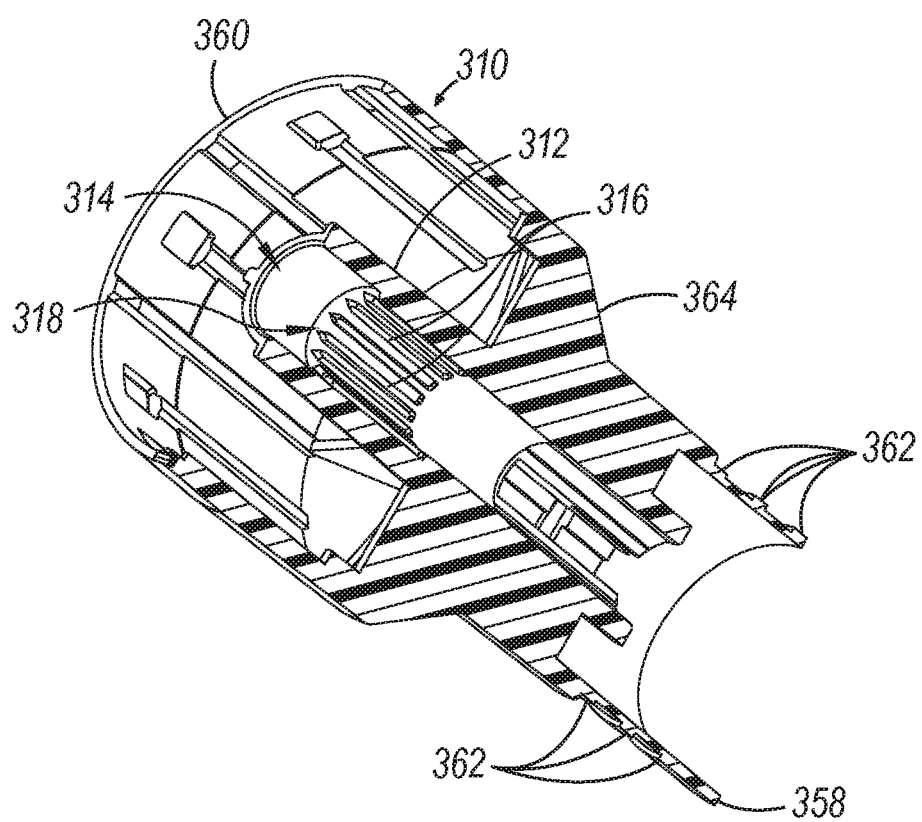
FIG. 10 depicts a perspective cross-sectional view of the body member of FIG. 9.

FIG. 9 shows a perspective view of an inner body member (310) of stapling head assembly (300) of FIG. 8. FIG. 10 shows a perspective cross-sectional view of inner body member (310) of FIG. 9. As shown in FIGS. 9-10, body member (312) of body member (310) defines a bore (314). A plurality of longitudinally extending splines (316) are equidistantly spaced in an angular array within bore (314). The distal ends of splines (316) include lead-in edges (318) that are configured to complement lead-in edges (428) of splines (426) on shank (420) of anvil (400). Body member (310) includes proximal and distal ends (358, 360). Proximal end (358) includes annular projections (362) for coupling body member (310) and outer shaft (210) together using a magneforming process as described below. Annular projections (362) are formed on an outer surface (364) of body member (310). Proximal end (358) also includes a tab (366).

Figure 11:
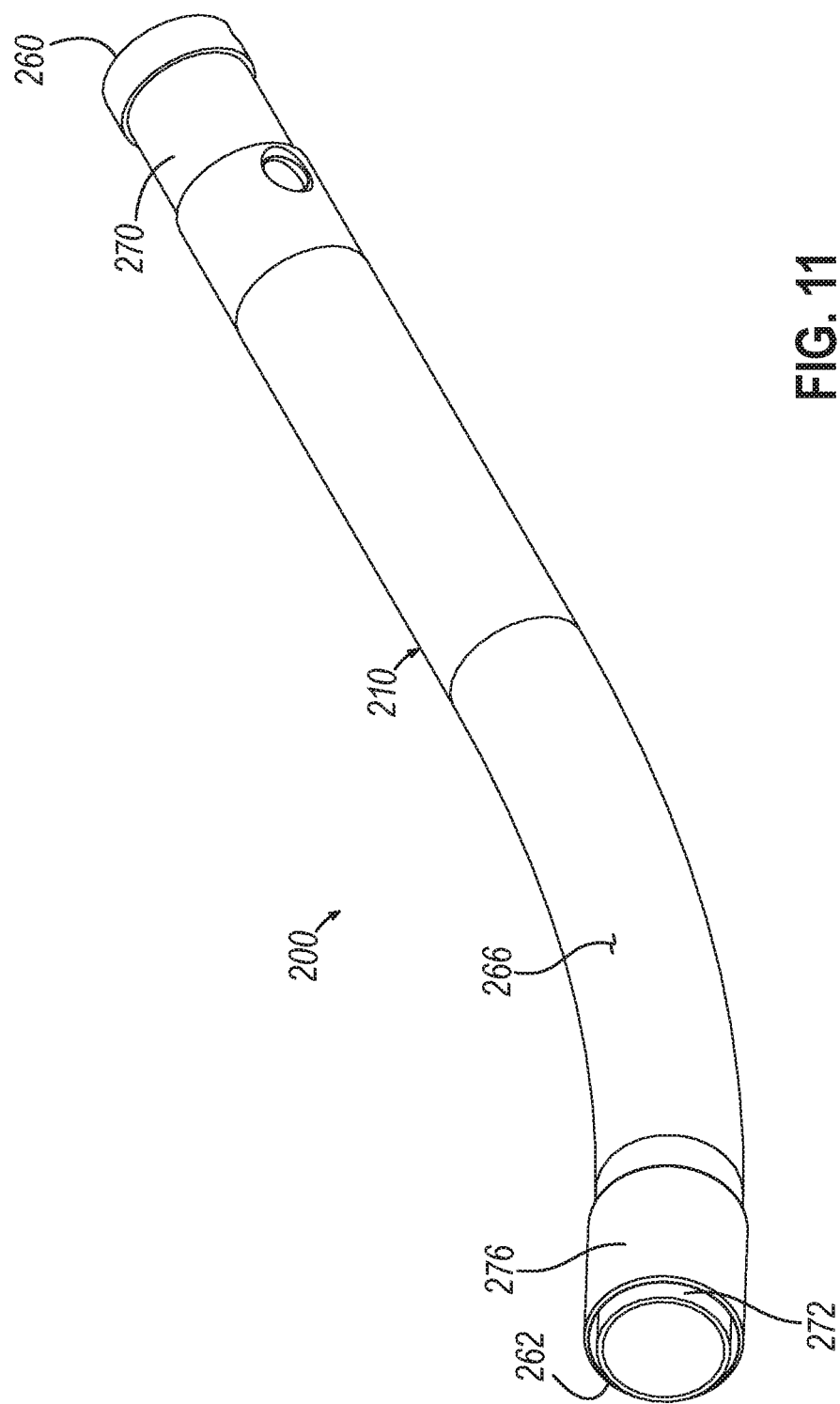
FIG. 11 depicts a perspective view of an outer shaft of the shaft assembly of FIG. 1.
Figure 12:
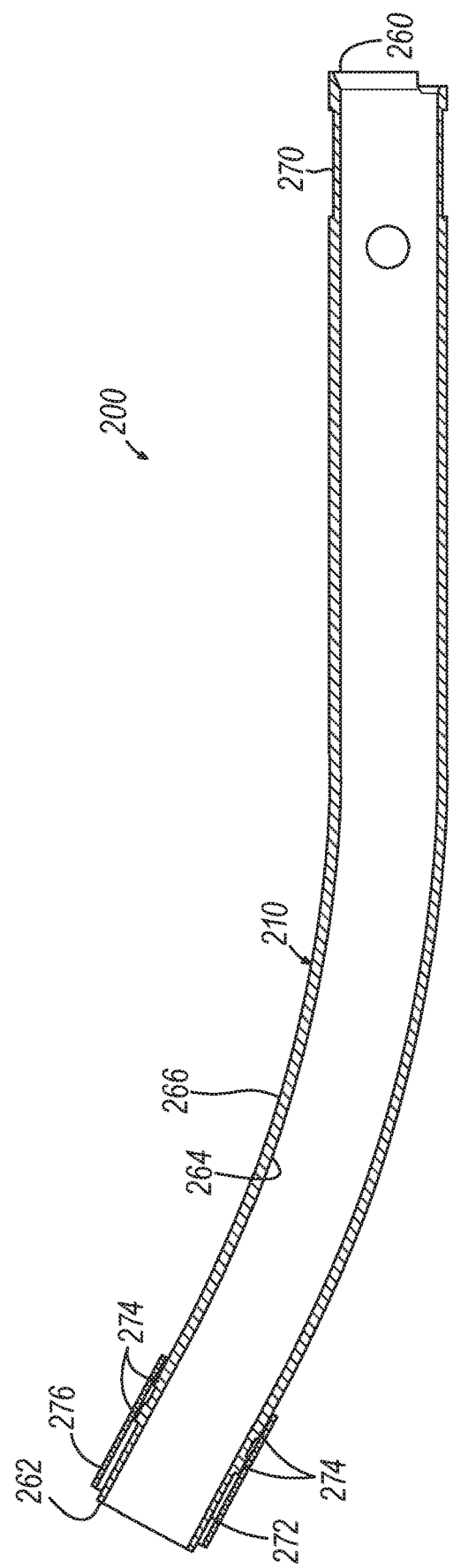
FIG. 12 depicts a cross-sectional side view of the outer shaft of FIG. 11.

FIG. 11 shows a perspective view of an outer shaft (210) of shaft assembly (200) of FIG. 1. FIG. 12 shows a perspective cross-sectional view of outer shaft (210) of FIG. 11. Outer shaft (210) includes proximal and distal ends (260, 262). Outer shaft (210) includes inner and outer surfaces (264, 266). Inner surface (264) defines a lumen (268). Outer shaft (210) also includes proximal and distal recessed surfaces (270, 272). Outer shaft (210) includes annular projections (274) disposed adjacent to distal end (262). FIG. 11 also shows a ferule (274) surrounding at least a portion of projections (274) and distal recessed surface (272).

C. Exemplary Anvil Coupling Detection

Figure 13B:
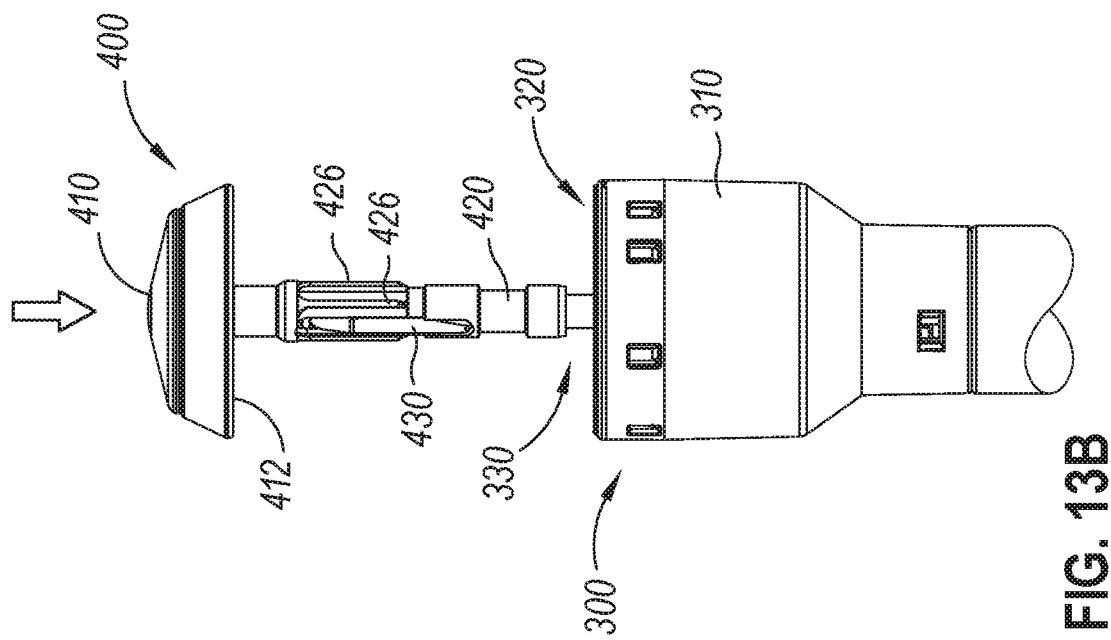
FIG. 13B shows a side elevational view of the anvil of FIG. 4 at a second longitudinal position in relation to the stapling head assembly of FIG. 7.
Figure 13A:
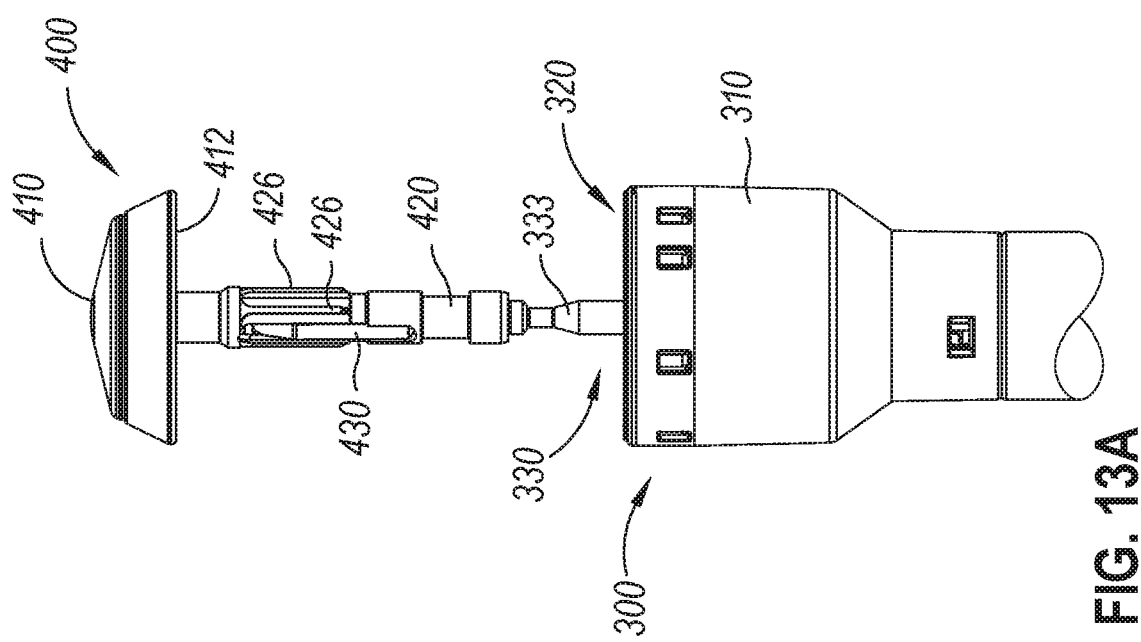
FIG. 13A shows a side elevational view of the anvil of FIG. 4 at a first longitudinal position in relation to the stapling head assembly of FIG. 7.

In some versions of instrument (10) it may desirable to provide instrument (10) with features that are configured to indicate proper and/or improper attachment of anvil (400) to trocar (330) of stapling head assembly (300). In the example shown in FIGS. 13A-13B, trocar (330) includes a colored region (333) that is longitudinally positioned at a location where colored region (333) is exposed before shank (420) is fully seated on trocar (330) (FIG. 13A); and covered when shank (420) is fully seated on trocar (330) (FIG. 13B).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

D. Exemplary Tissue Gripping Features

It may be desirable to provide a version of stapling head assembly (300) that includes features that enhance gripping of tissue during actuation of stapling head assembly (300), thereby promoting successful tissue cutting and staple deployment, without increasing the risk of damaging the patient's tissue as stapling head assembly (300) slides along the tissue during positioning of stapling head assembly (300). By way of further example only, one such deck member is shown and described in U.S. application Ser. No. 16/583,690, entitled "Circular Surgical Stapler," filed Sep. 26, 2019, issued as U.S. Pat. No. 11,123,075 on Sep. 21, 2021, the disclosure of which is incorporated by reference herein.

V. Exemplary Clamping and Firing Sequence

Figure 14A:
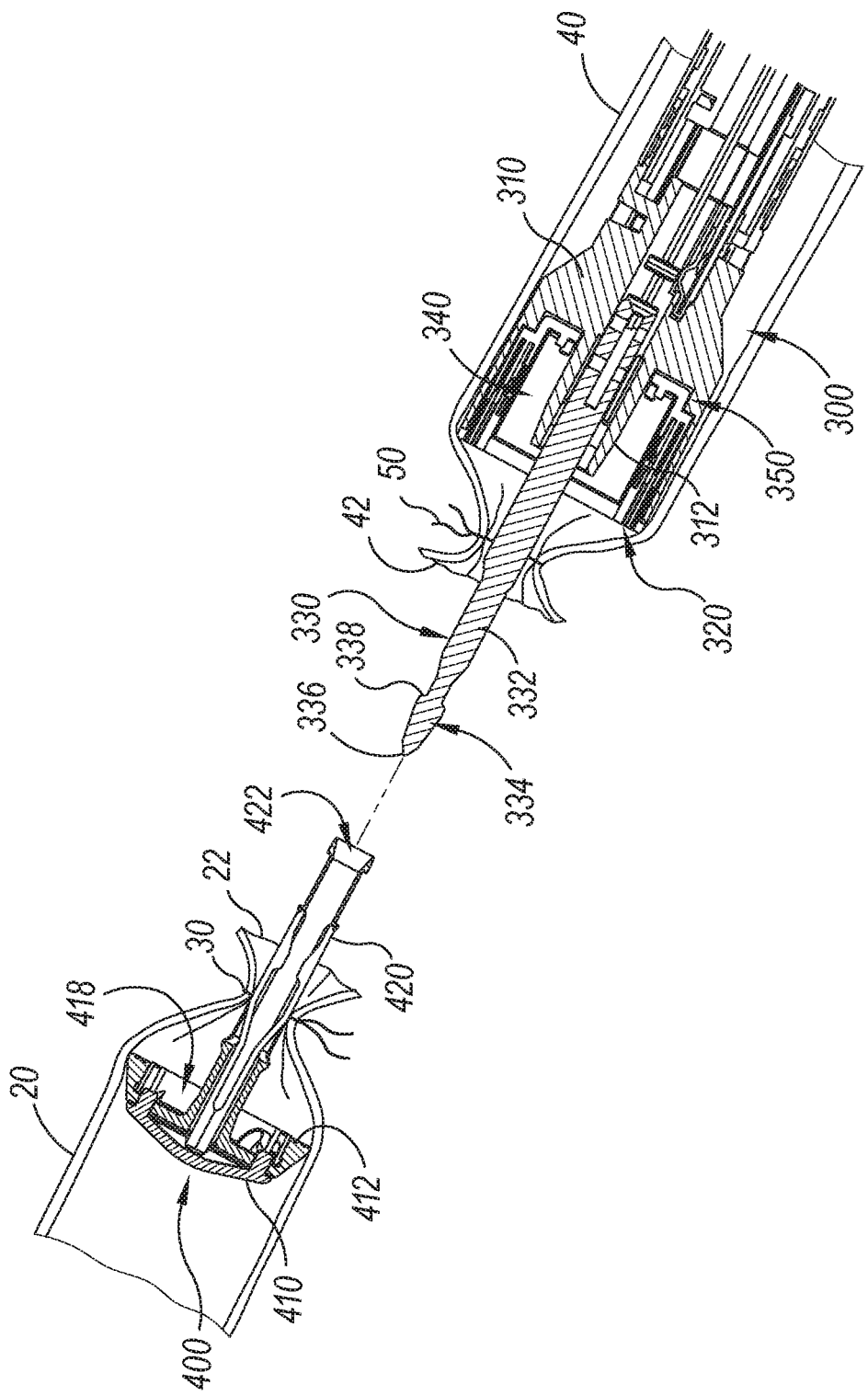
FIG. 14A depicts a cross-sectional side view of the anvil of FIG. 4 positioned within a first section of a digestive tract and the stapling head assembly of FIG. 7 positioned in a second section of the digestive tract, with the anvil separated from the stapling head assembly.

FIGS. 14A-14E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 14A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 14A-14E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 14A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). In some other variations, purse-string suture (30) is tightened around the proximal end of shank (420). In some such variations, the proximal end of shank (420) may include a notch or other feature to securely capture purse-string suture (30). Continuing with the present example, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 14B:
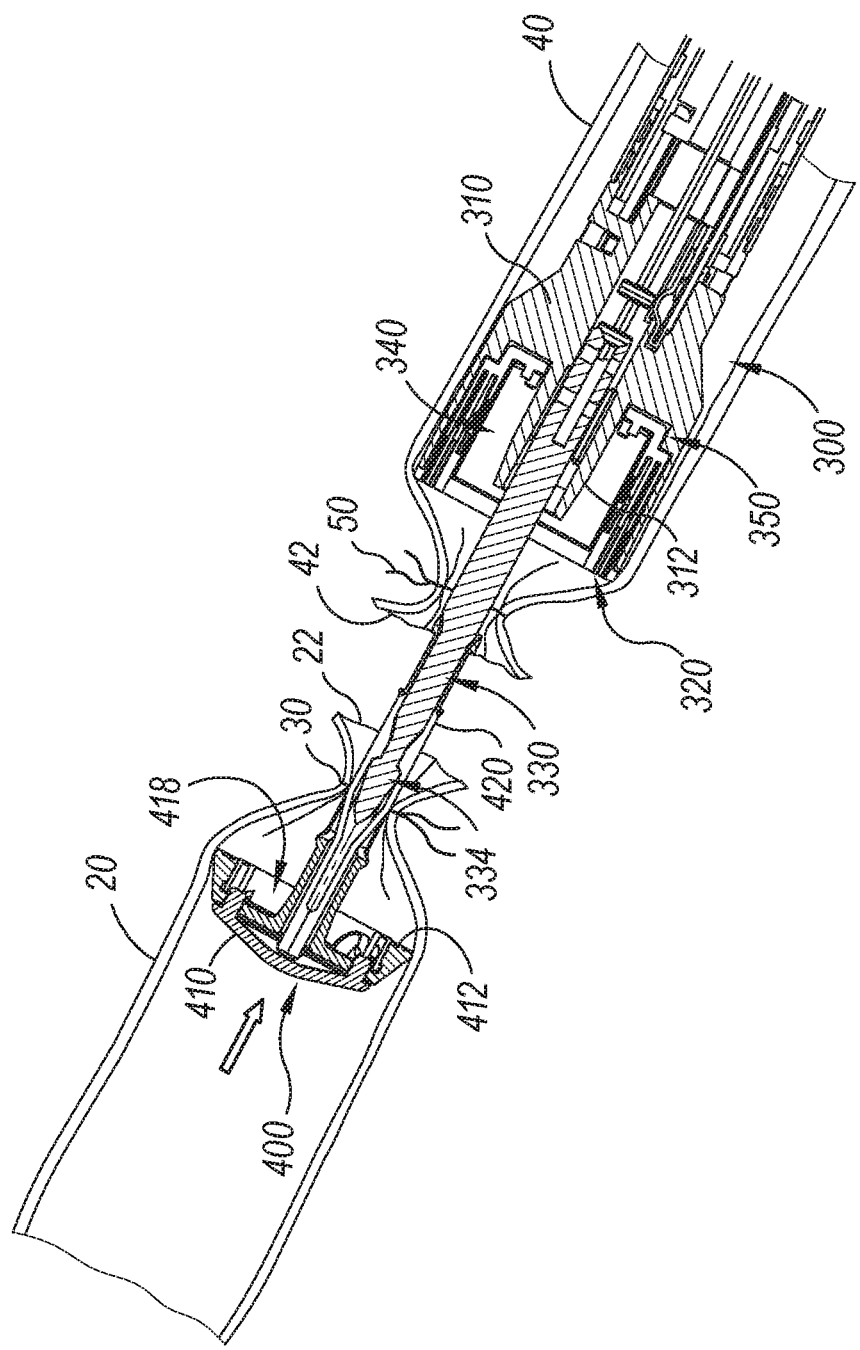
FIG. 14B depicts a cross-sectional side view of the anvil of FIG. 4 positioned within the first section of the digestive tract and the stapling head assembly of FIG. 7 positioned in the second section of the digestive tract, with the anvil secured to the stapling head assembly.
Figure 14C:
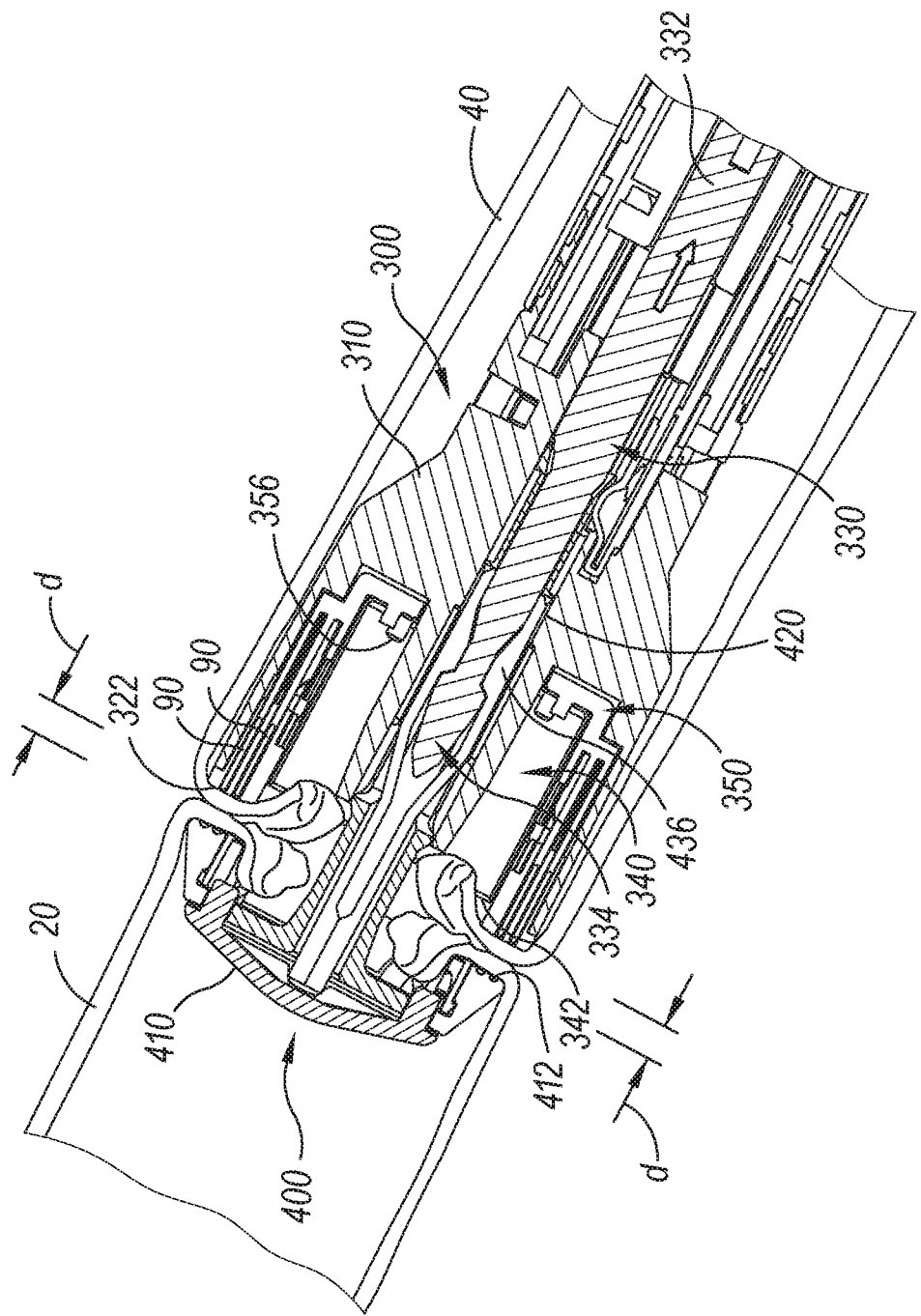
FIG. 14C depicts a cross-sectional side view of the anvil of FIG. 4 positioned within the first section of the digestive tract and the stapling head assembly of FIG. 7 positioned in the second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 14B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 14C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may use user feedback feature (114) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator actuates safety trigger (140) to enable actuation of firing trigger (150). The operator then actuates firing trigger (150). This actuates stapling head assembly (300) by driving knife member (340) and staple driver member (350) distally as shown in FIG. 13D. As knife member (340) translates distally, cutting edge (342) of knife member (340) cuts excess tissue that is positioned within annular recess (418) of anvil (400) and the interior of knife member (340).

As shown in FIG. 5, anvil (400) of the present example includes a breakable washer (417) within annular recess (418). This washer (417) is broken by knife member (340) when the knife member (340) completes a full distal range of motion from the position shown in FIG. 14C to the position shown in FIG. 14D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue.

Figure 14D:
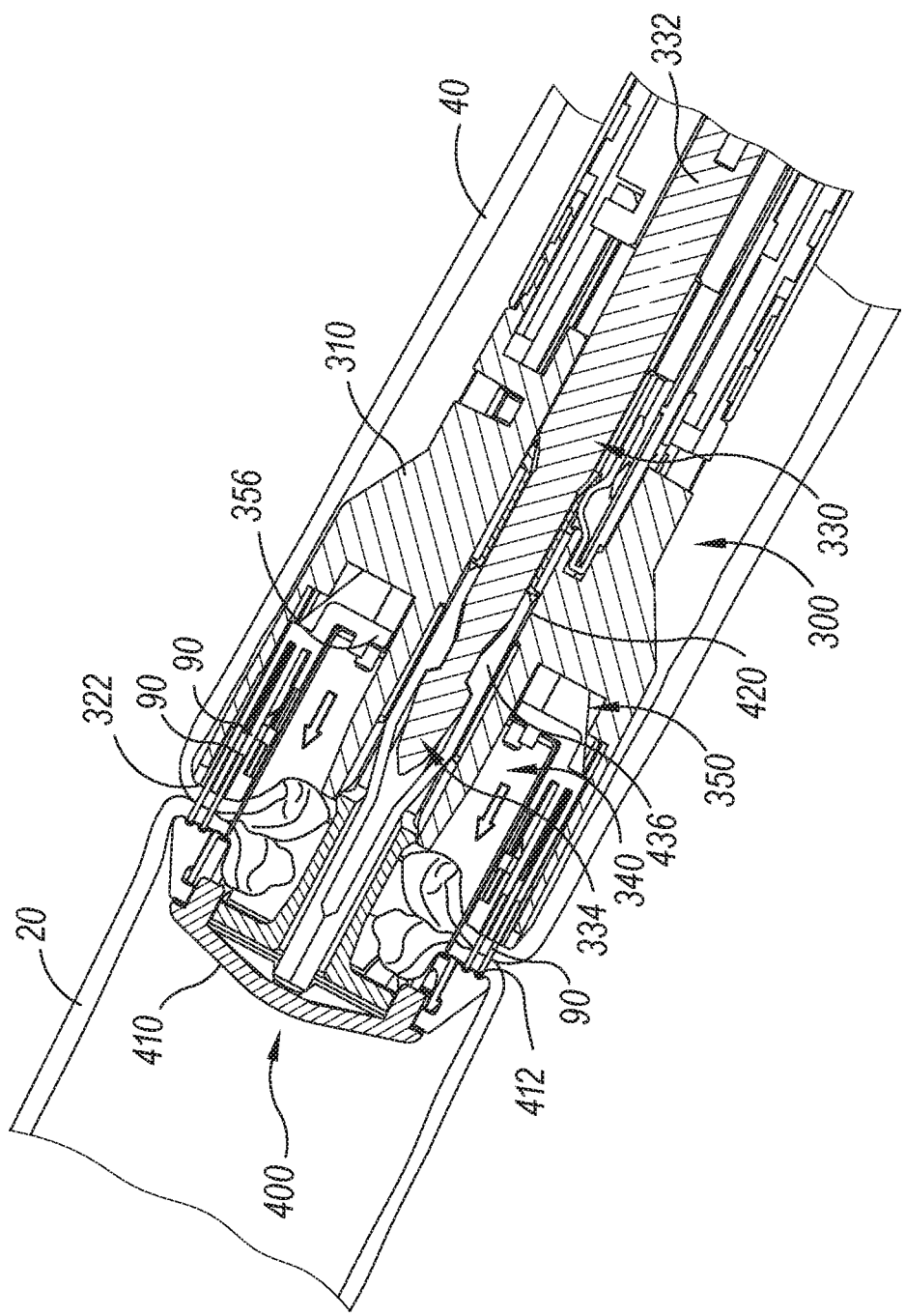
FIG. 14D depicts a cross-sectional side view of the anvil of FIG. 4 positioned within the first section of the digestive tract and the stapling head assembly of FIG. 7 positioned in the second section of the digestive tract, with the stapling head assembly actuated to sever and staple the clamped tissue.

As staple driver member (350) translates distally from the position shown in FIG. 14C to the position shown in FIG. 14D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art; or into a three-dimensional shape. In either case, the formed staples (90) secure the ends of tissue together.

Figure 14E:
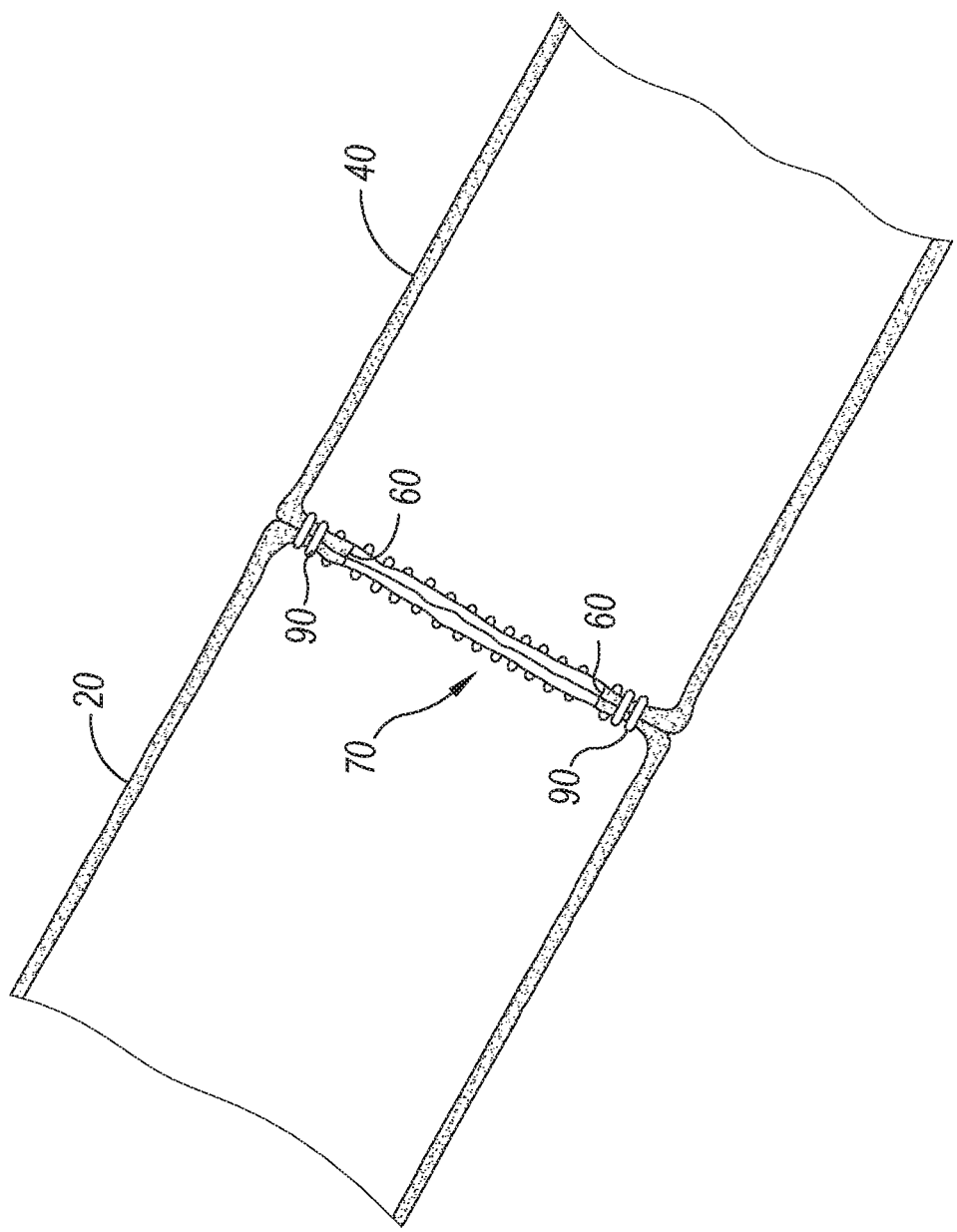
FIG. 14E depicts a cross-sectional side view of the first and second sections of the digestive tract of FIG. 14A joined together at an end-to-end anastomosis.

After the operator has actuated stapling head assembly (300) as shown in FIG. 14D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 14E. The inner diameter of the anastomosis (70) is defined by the severed edge (60) left by knife member (340).

VI. Exemplary Coupling of Shaft Assembly with Stapling Head Assembly

As previously described, shaft assembly (200) may be coupled with stapling head assembly (300). Particularly, outer shaft (210) of shaft assembly (200) may be coupled together with body member (310) of stapling head assembly (300) using a magneforming process. Magneforming, also called electromagnetic forming (EM forming), is a high velocity, cold forming process for electrically conductive metals. For example, electrically conductive metals may include copper and aluminum. The workpiece is reshaped by high intensity pulsed magnetic fields that induce a current in the workpiece and a corresponding repulsive magnetic field, rapidly repelling portions of the workpiece. As a result, a desired portion of the workpiece may be suitably shaped without contact from a tool, although in some versions, the workpiece may be pressed against a die.

Regarding instrument (10), outer shaft (210) and body member (310) may be aligned with ferule (276) disposed over annular projections (274) of outer shaft (210) and annular projections (362) of body member (310). Once ferule (276) is aligned, a magneform machine may apply a magnetic field to crimp ferule (276) (e.g., aluminum sleeve) over annular projections (274) of outer shaft (210) and annular projections (362) of body member (310). This crimping of ferule (276) couples outer shaft (210) and body member (310) together. However, the magneform machine may be expensive, bulky, and utilize a significant amount of energy to create a magnetic field to suitably crimp ferule (276). The amount of energy produced by the magneform and the location of where the magnetic field is concentrated may make it more difficult to produce acceptable crimping grooves in ferule (276) to couple outer shaft (210) and body member (310) together. Additionally, the fixturing may limit the manner in which outer shaft (210) and body member (310) are held. Scrap may also be produced on the assembly line due to the fixturing to create the magnetic field. Additionally, body member (310) may stick during the preloading process that occurs before the magnetic field of the magneform is applied.

As a result, it may be desirable to form a suitable coupling between outer shaft (210) and body member (310) that eliminates the magneforming step involving the magneforming machine and the associated magnetic field and ferule (276). Exemplary versions of such an alternative coupling are described below in connection with FIGS. 15-27. Each exemplary alternative coupling is shown in combination with an instrument body (shown as handle assembly (100) in FIGS. 1-3), a shaft assembly (500, 700) in place of shaft assembly (200), and a stapling head assembly (600, 800) in place of stapling head assembly (300). As described in greater detail below, an exemplary body member (610, 810) (also referred to as a "casing") of stapling head assembly (600, 800) may be coupled with an exemplary outer shaft (510, 710) of shaft assembly (500, 700) using exemplary coupling features (528, 672, 728, 872). Coupling features (528, 672, 728, 872) may provide a higher tensile strength configured to withstand higher tensile loads than the coupling features formed by magneforming process described above. As such, coupling feature (528, 728) of outer shaft (510, 710) and coupling feature (672, 872) of body member (610, 810) may eliminate the use of the magneforming step described above.

A. First Exemplary Alternative Coupling

1. Overview

Figure 15:
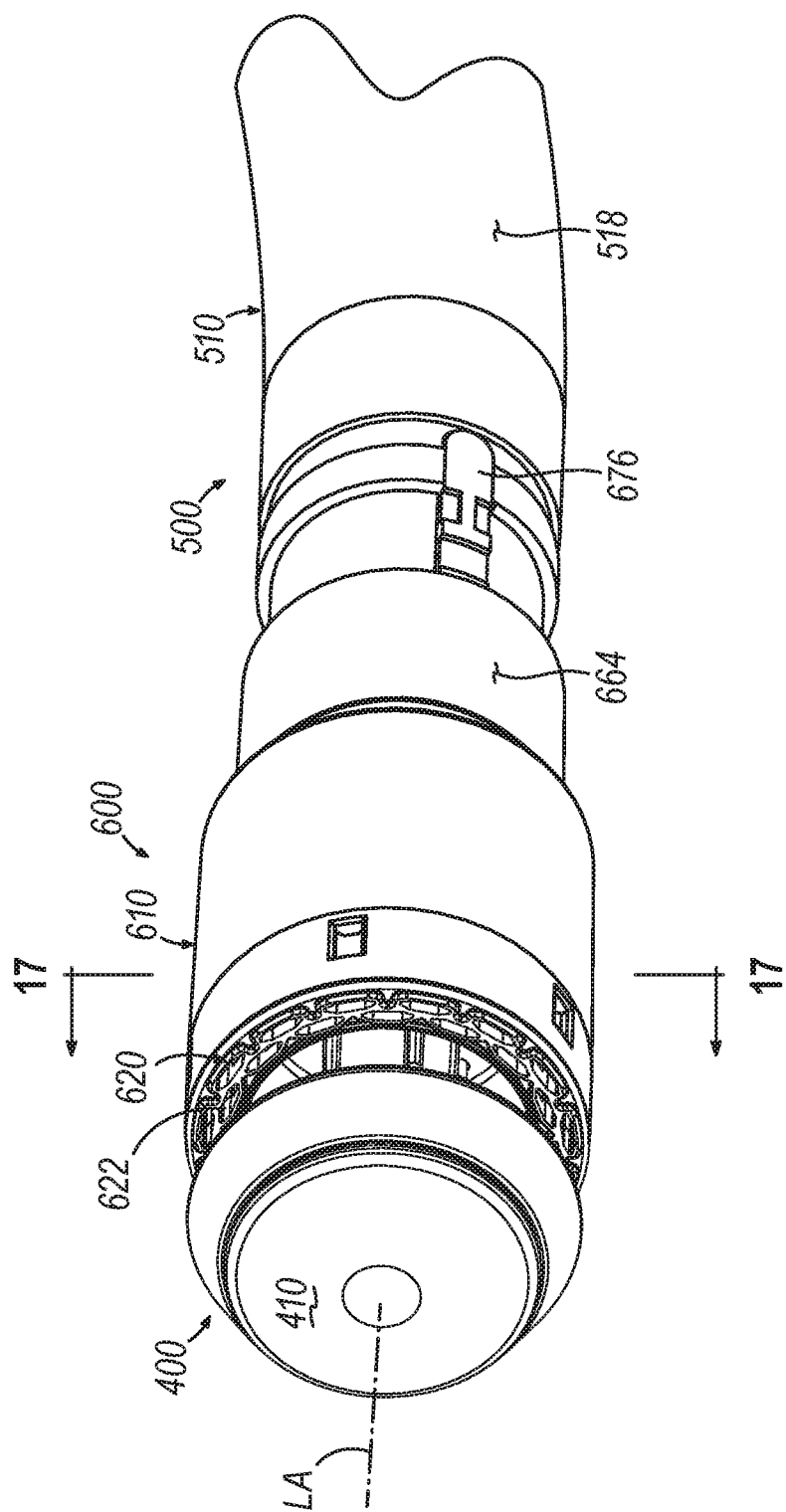
FIG. 15 depicts a perspective view of a first exemplary alternative stapling head assembly coupled with a first exemplary alternative shaft assembly that may be incorporated into the circular stapler of FIG. 1, with the stapling head assembly being coupled with the anvil of FIG. 4.
Figure 16:
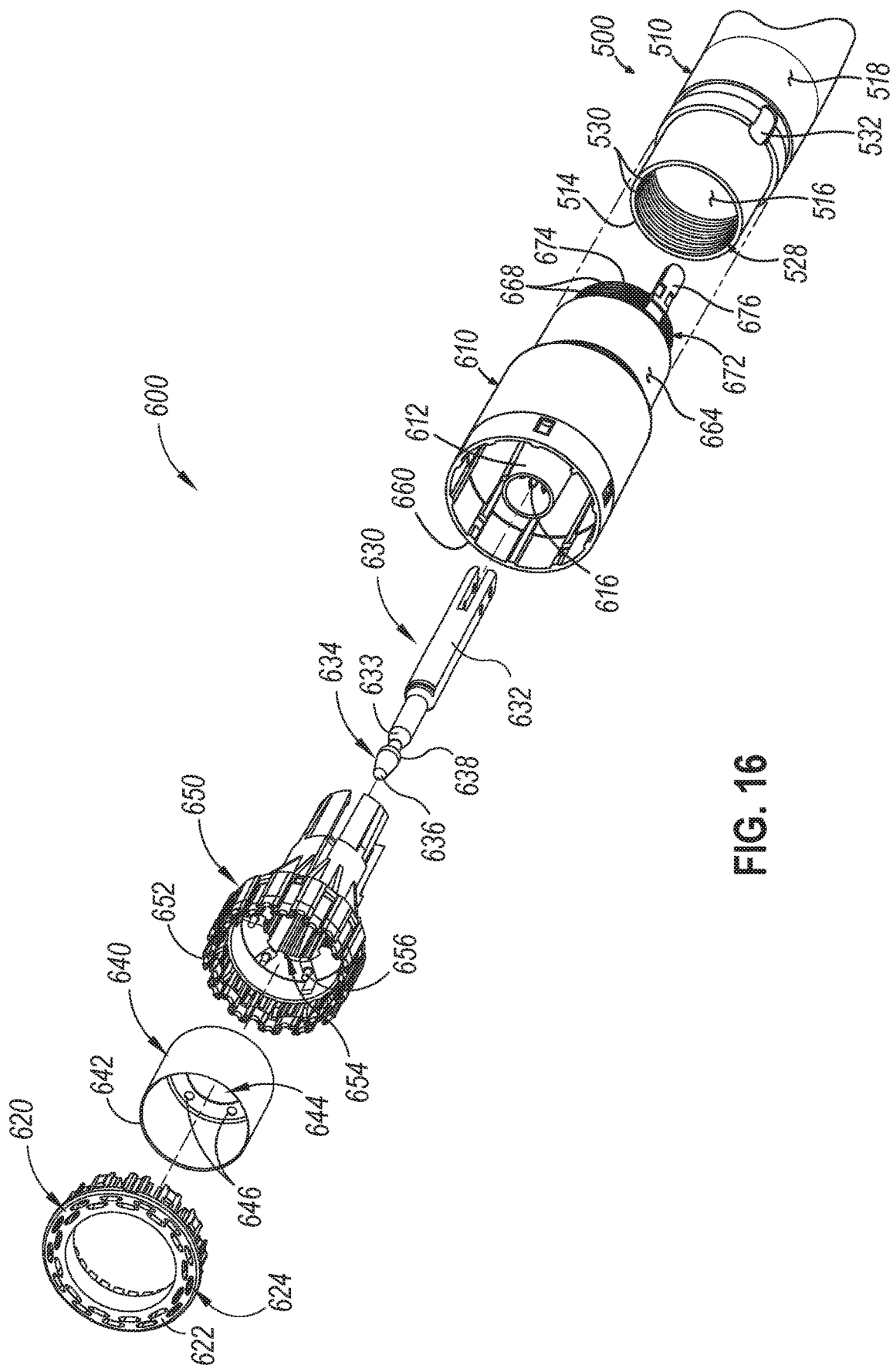
FIG. 16 depicts an exploded perspective view of the stapling head assembly and a distal portion of the shaft assembly of FIG. 15, showing a first exemplary alternative body member of the stapling head assembly and a first exemplary alternative outer shaft of the shaft assembly of FIG. 15, with the body member and the outer shaft including first exemplary coupling features.
Figure 17:
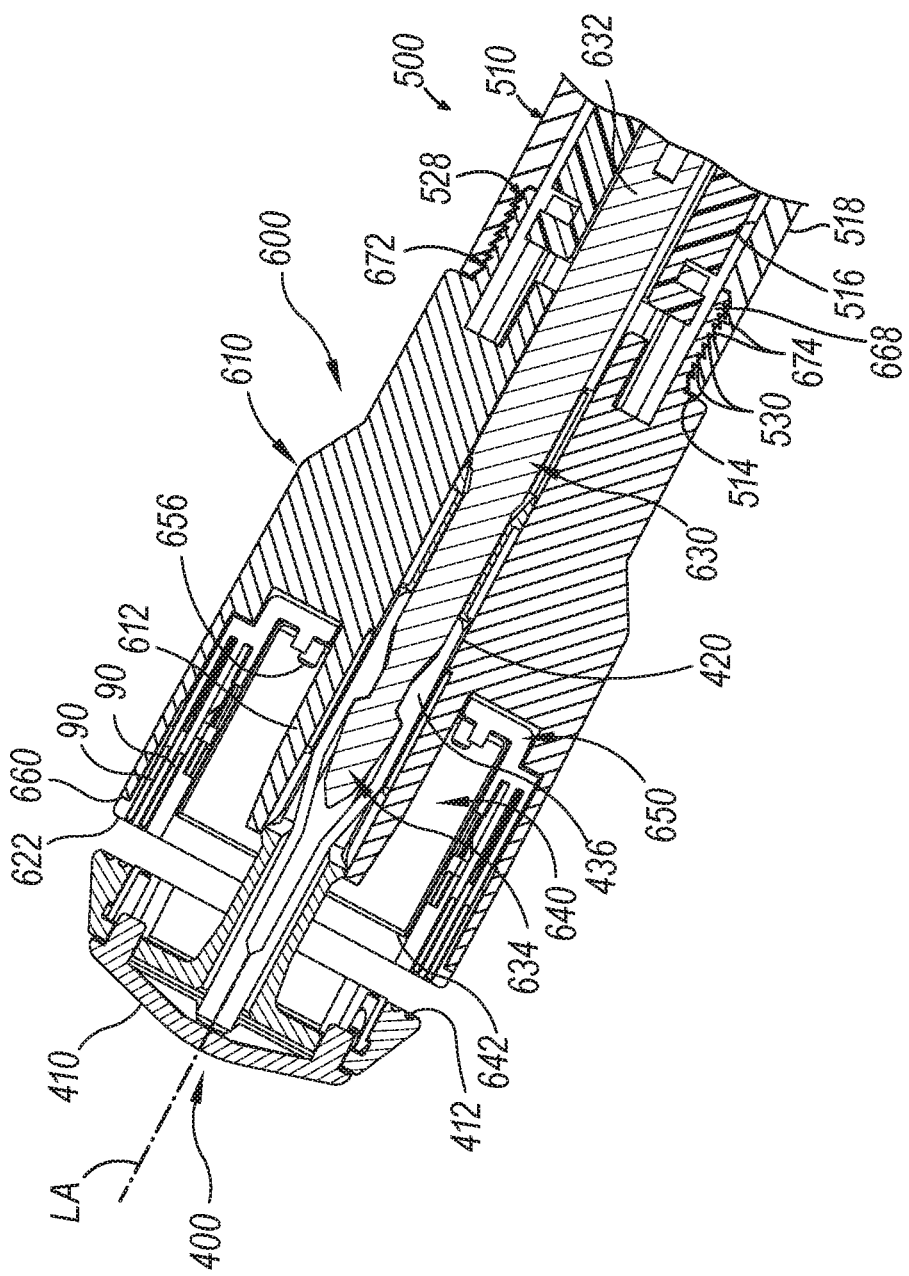
FIG. 17 depicts a cross-sectional side view of the stapling head assembly and the shaft assembly of FIG. 15 taken along line 17-17 of FIG. 15, with the body member being coupled together with the outer shaft using the coupling features of FIG. 16.

FIGS. 15-22 show a first exemplary alternative shaft assembly (500) coupled with a first exemplary alternative stapling head assembly (600). Particularly, FIG. 15 shows shaft assembly (500) coupled with stapling head assembly (600), as well as anvil (400) previously described with reference to FIGS. 4-6 coupled with stapling head assembly (600). FIG. 16 shows an exploded perspective view of a first exemplary alternative outer shaft (510) of shaft assembly (500) and a first exemplary alternative body member (610) of stapling head assembly (600) of FIG. 15. FIG. 17 shows a cross-sectional side view of shaft assembly (500) and stapling head assembly (600) of FIG. 15 taken along line 17-17 of FIG. 15, with outer shaft (510) being coupled with body member (610).

Outer shaft (510) and body member (610) may be incorporated into a modified version of instrument (10), which may include a body (shown as handle assembly (100) in FIGS. 1-3), an anvil (shown as anvil (400), a shaft (shown as shaft assembly (500)), and a stapling head assembly (600). Outer shaft (510) and body member (610) of this example are configured and operable like outer shaft (210) and body member (310), with differences described below. For example, outer shaft (510) may be insertable into shaft assembly (200) in place of outer shaft (210). Similarly, body member (610) may be insertable into stapling head assembly (300) in place of body member (310).

Figure 18:
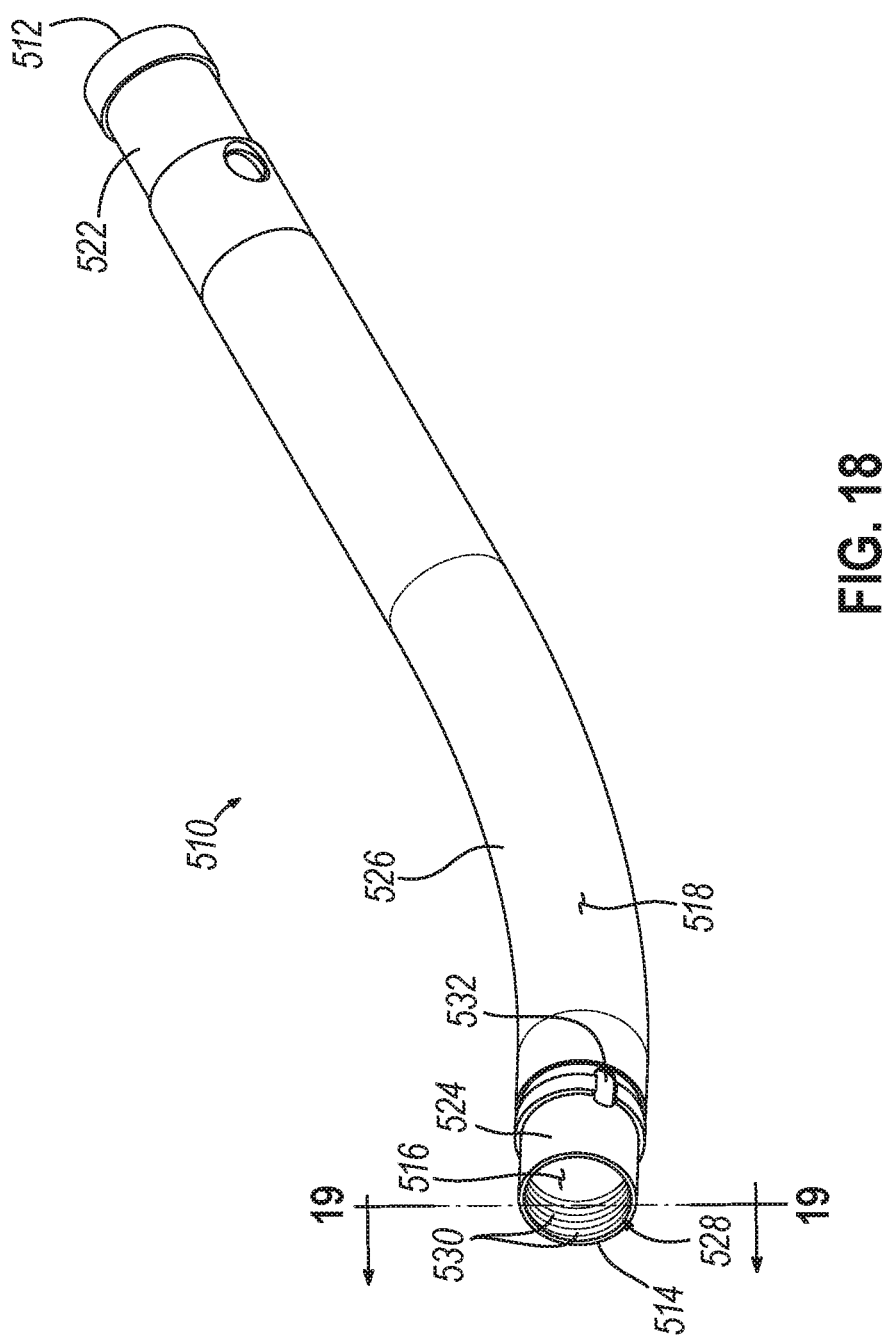
FIG. 18 depicts a perspective view of the outer shaft of the shaft assembly of FIG. 16.
Figure 19:
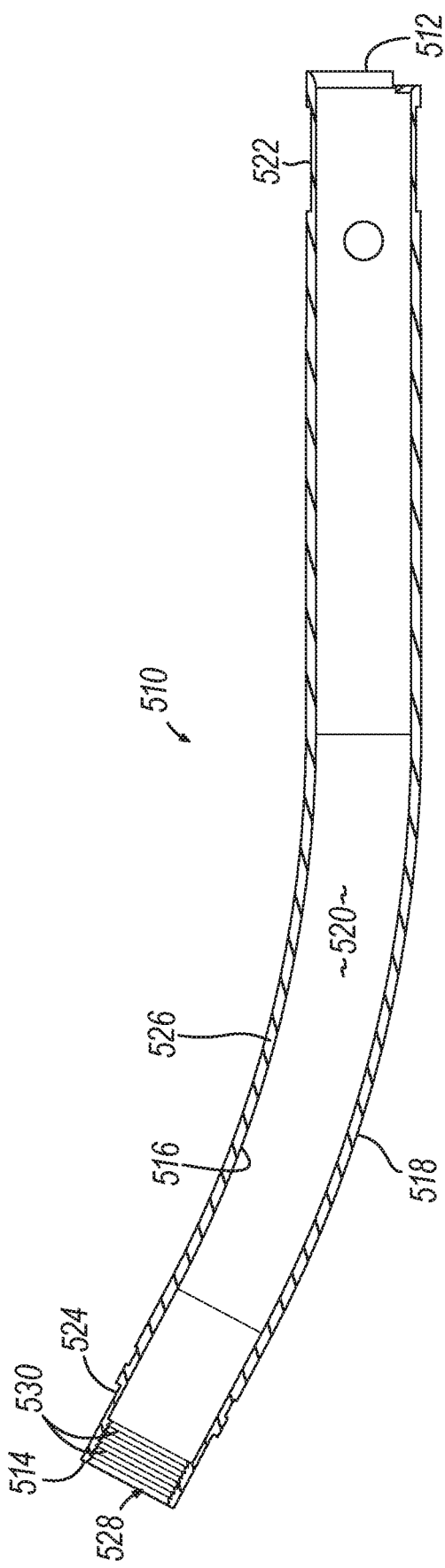
FIG. 19 depicts a cross-sectional side view of the outer shaft of FIG. 18 taken along line 19-19 of FIG. 18.

2. First Exemplary Alternative Shaft Assembly Including First Exemplary Alternative Outer Shaft As shown in FIGS. 15-17, shaft assembly (500) extends between handle assembly (100) and stapling head assembly (600). FIGS. 18-19 show outer shaft (510) in additional detail. Particularly, FIG. 18 shows a perspective view of outer shaft (510) of shaft assembly (500) of FIG. 16, and FIG. 19 shows a cross-sectional side view of outer shaft (510) of FIG. 18 taken along line 19-19 of FIG. 18. Outer shaft (510) includes proximal and distal ends (512, 514). Outer shaft (510) includes inner and outer surfaces (516, 518). Inner surface (516) defines a lumen (520). Outer shaft (510) also includes proximal and distal recessed surfaces (522, 524). Outer shaft (510) is tubular and may include a preformed bend (526).

Outer shaft (510) includes a coupling feature (528). Coupling feature (528) includes at least one barb (530). As shown, coupling feature (528) of the present example includes a plurality of annular barbs (530) that are spaced equidistantly from one another in an axial direction. While barbs (530) are shown as being annular and extending completely around the circumference of inner surface (516), it is also envisioned that barbs (530) may have a variety of other suitable shapes and sizes. Inner surface (516) of outer shaft (510) includes barbs (530) of outer shaft (510). Outer shaft (510) also includes a tab receiving portion (532) configured to receive tab (676) to assist with rotational alignment of outer shaft (510) and body member (610).

Similar to shaft assembly (200), and though not shown in FIGS. 15-17, shaft assembly (500) further includes a trocar actuation rod (similar to trocar actuation rod (220)) and a trocar actuation band assembly (similar to trocar actuation band assembly (230)) which are shown in FIG. 3. The distal end of trocar actuation band assembly (230) may be fixedly secured to the proximal end of a shaft (632) of a trocar (630). The proximal end of trocar actuation band assembly (230) is fixedly secured to the distal end of trocar actuation rod (220). Trocar (630) translates longitudinally relative to outer shaft (210) in response to translation of trocar actuation band assembly (230) and trocar actuation rod (220) relative to outer shaft (510).

3. First Exemplary Stapling Head Assembly Including First Exemplary Alternative Body Member As shown in FIGS. 15-17, stapling head assembly (600) may be operable to drive at least one annular array of staples (90) though tissue similar to stapling head assembly (300). As shown, stapling head assembly (600) comprises body member (610), a deck member (620), an anvil coupling feature (shown as trocar (630)), a knife member (640), a staple driver member (650), and at least one annular array of staples (90). Stapling head assembly (600) defines a longitudinal axis (LA). Stapling head assembly (600) is positioned at distal end (514) of outer shaft (510) of shaft assembly (500). Stapling head assembly (600) is configured to cut and staple tissue Stapling head assembly (600) may be coupled with anvil (400) as shown and described with reference to FIGS. 4-6. Anvil (400) is configured to couple with anvil coupling feature (shown as trocar (330)). Anvil (400) is configured to deform at least one annular array of staples (90) driven by staple driver member (650). Staple driver member (650) is operable to drive at least one annular array of staples (90) though tissue.

Similar to deck member (320), deck member (620) is fixedly secured to body member (610). Deck member (620) includes a distally presented deck surface (622) defining two concentric annular arrays of staple openings (624). Staple openings (624) are arranged to correspond with the arrangement of staple drivers (652) of staple driver member (650) and staple forming pockets (414) of anvil (400) described above. Staple driver member (650) is similar to staple driver member (350) described in detail above. Deck member (620) is configured to allow knife member (640) to translate distally to a point where cutting edge (642) is distal to deck surface (622). Similar to trocar (330), when trocar (630) is secured to shank (420) and trocar (630) is retracted proximally, the inner diameter of a bore (614) of an inner core member (612) of body member (610) laterally constrains latch members (430) to maintain engagement between latch shelves (436) and proximal surface (638) of a head (634) of trocar (630).

Similar to knife member (340), knife member (640) is coaxially positioned within staple driver member (650). Knife member (640) includes a distally presented, sharp circular cutting edge (642) configured to cut through tissue. Knife member (640) is sized such that knife member (640) defines an outer diameter that is smaller than the diameter defined by the inner annular array of staple drivers (652). Knife member (640) also defines an opening (644) that is configured to coaxially receive inner core member (612) of body member (610). An annular array of openings (646) formed in knife member (640) is configured to complement the annular array of studs (656) of staple driver member (650), such that knife member (640) is fixedly secured to staple driver member (650) via studs (656) and openings (646). The arrangement of studs (656) of staple driver member (650) and openings (646) of knife member (640) may vary from studs (456) of staple driver member (450) and openings (446) of knife member (440) described above. By way of example only, studs (456, 656) may be heat staked to knife member (640) using techniques known in the art. Alternatively, the knife member and the staple driver member may be coupled together using any one or more of the teachings disclosed in U.S. patent application Ser. No. No. 16/887,140, entitled "Knife for Circular Surgical Stapler," filed on May 29, 2020, issued as U.S. Pat. No. 11,426,171 on Aug. 30, 2022.

Figure 20:
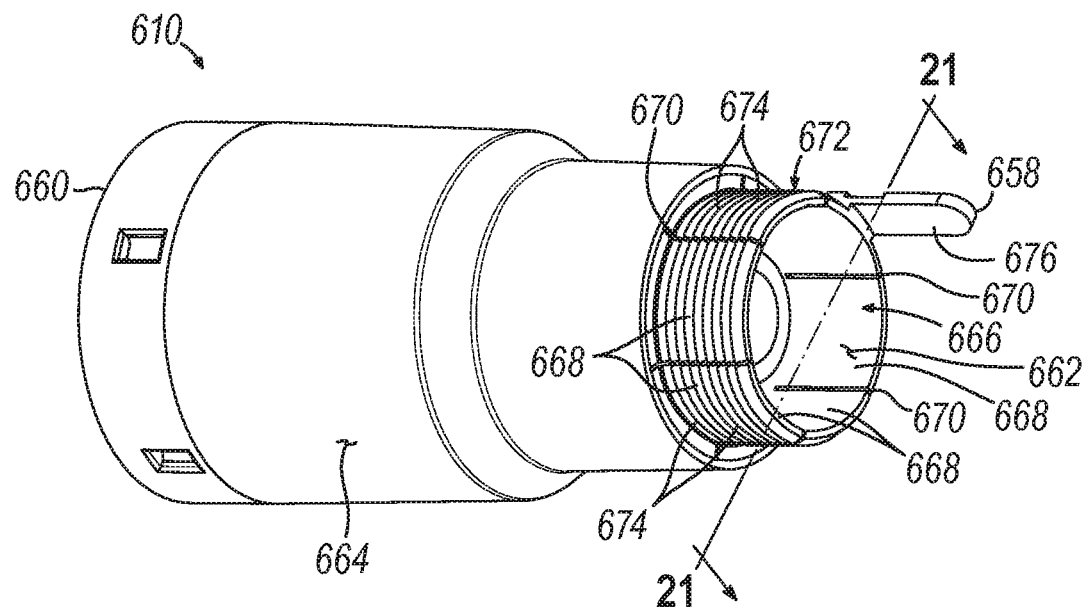
FIG. 20 depicts a perspective view of the body member of the stapling head assembly of FIG. 16.
Figure 21:
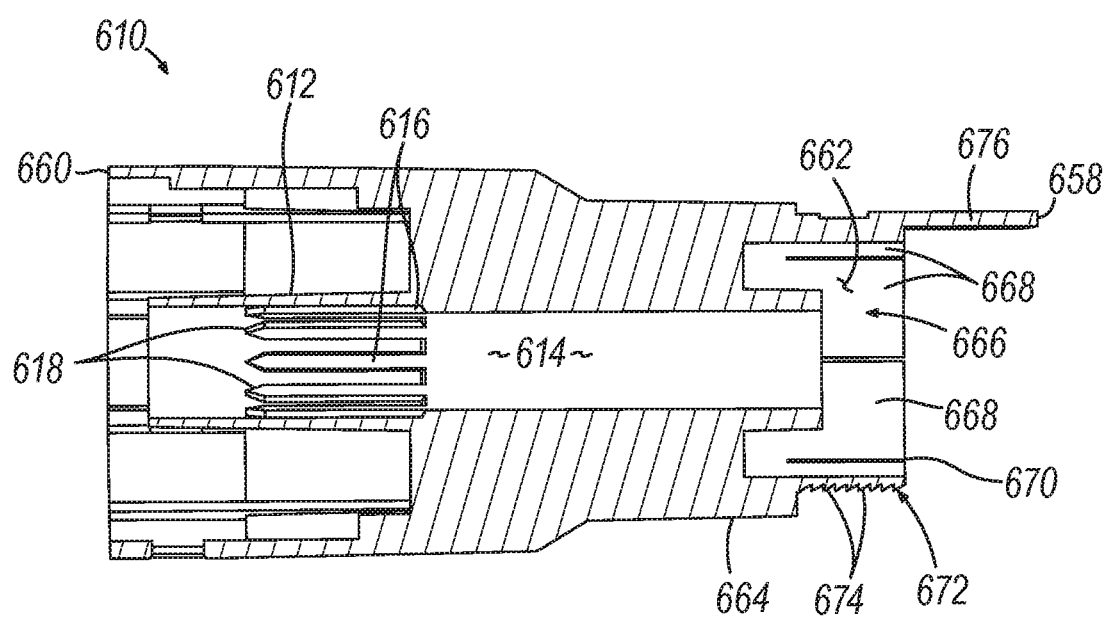
FIG. 21 depicts a cross-sectional view of the body member of FIG. 20 taken along line 21-21 of FIG. 20.

Body member (610) is similar to body member (310), with differences described below with reference to FIGS. 20-22. FIG. 20 shows a perspective view of body member (610) of stapling head assembly (600) of FIG. 16. FIG. 21 shows a cross-sectional side view of body member (610) of FIG. 20 taken along line 21-21 of FIG. 20. Body member (610) may house staple driver member (650) and knife member (640). A plurality of longitudinally extending splines (616) are equidistantly spaced in an angular array within bore (614). The distal ends of splines (616) include lead-in edges (618) that are configured to complement lead-in edges (428) of splines (426) on shank (420) of anvil (400). Similar to inner core member (312), inner core member (612) of body member (610) defines bore (614) configured to receive staple driver member (650) at least partially therein. This engagement prevents anvil (400) from being released from trocar (630) during firing of stapling head assembly (600). In particular, after shank (420) is secured to trocar (630), and as anvil (400) is thereafter retracted proximally relative to stapling head assembly (600), lead-in edges (428, 618) may cooperatively engage each other to drive anvil (400) to rotate relative to trocar (630) to angularly align splines (426) of anvil (400) with the gaps between splines (616) of body member (610). Thus, splines (426, 616) are configured to cooperate with each other to ensure that staples ejected through staple openings (624) are accurately driven into corresponding staple forming pockets (414) on a consistent basis, regardless of the angular orientation of anvil (400) relative to stapling head assembly (600) at the time anvil (400) is initially secured to trocar (630). Splines (426, 616) are configured to engage each other to provide a predetermined angular alignment between anvil (400) and stapling head assembly (600).

Body member (610) includes proximal and distal ends (658, 660). Body member (610) includes inner and outer surfaces (662, 664). Inner surface (662) defines a cavity (666) that may be concentrically aligned with bore (614) along longitudinal axis (LA). As shown, body member (610) includes a plurality of arms (668) disposed generally adjacent proximal end (658). Arms (668) may be separated by slots (670) that extend distally such that each arm (668) may resiliently deflect in a radial direction relative to one or more adjacent arms (668) when body member (610) is joined with outer shaft (510) in the manner described below. While six arms (668) separated by six slots (670) are shown, more or fewer arms (668) and/or slots (670) are also envisioned. Each arm (668) may have the same or different shape and/or size. Similarly, each slot (670) may have the same or different shape and/or size. Shaft member (510) and body member (610) may be formed from a polymer material. One such suitable polymer material may have a filler content (ash) of between approximately 38-42%, a tensile strength of approximately 38,000 psi, a tensile modulus of approximately 4,000,000 psi, a flexural modulus of approximately 3,100,000 psi, an Izod impact notched (73F) of 1.4 ft-lb/in, and a specific gravity of between approximately 1.3-1.36 g/cubic cm.

Body member (610) includes at least one coupling feature (672) that is configured to mechanically couple with coupling feature (528) of outer shaft (510). Coupling feature (672) of the present example includes at least one annular barb (674). As shown, barbs (674) are spaced equidistantly from one another in an axial direction. Barbs (674) of body member (610) are circumferentially disposed on each of respective arms (668). While barbs (674) are shown as being generally annular except for slots (670) and disposed on arms (668), it is also envisioned that barbs (674) may have a variety of suitable shapes and sizes. As shown in FIG. 17, barbs (674) of arms (668) may be lockingly engaged with barbs (530) of outer shaft (510). For example, at least one barb (674) of body member (610) may couple with at least one barb (530) of outer shaft (510) using a frictional push fit. Barbs (674) of body member (610) may include ratcheting barbs. Barbs (530, 674) may be coupled together by translating at least one of outer shaft (510) or body member (610) relative to the other of outer shaft (510) or body member (610). Coupling feature (672) of body member (610) may form a one-way permanent connection with coupling feature (528) of outer shaft (510), such that coupling features (528, 672) do not allow for separation of outer shaft (510) and body member (610) once coupled together.

Figure 22:
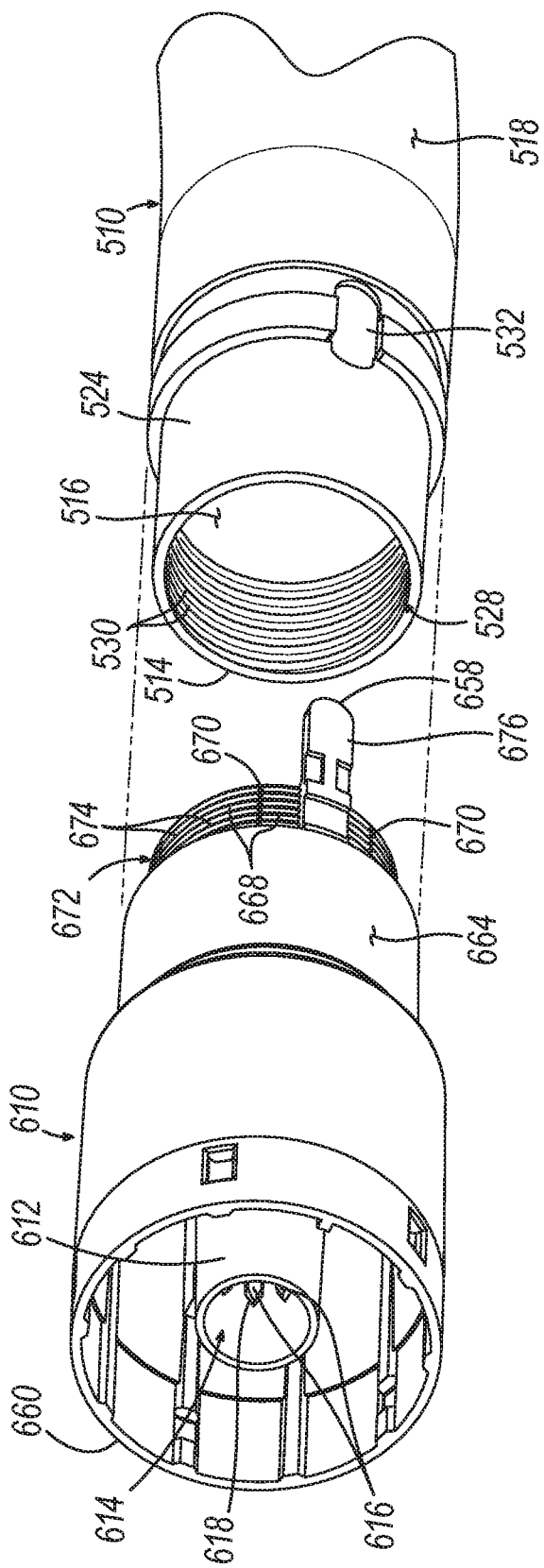
FIG. 22 depicts a perspective view of the outer shaft and the body member of FIG. 16.

FIG. 22 shows a perspective view of body member (610) and outer shaft (510) of FIG. 16. As shown, barbs (674) are disposed on outer surface (664) of body member (610) to suitably couple with barbs (530) disposed on inner surface (516) of outer shaft (510). Alternatively, barbs (530) may be disposed on outer surface (518) of outer shaft (510) with corresponding barbs (530) of body member (610) being disposed on inner surface (662) of body member (610). One or more arms (668) of body member (610) may deflect radially inwardly, then reflect radially outwardly upon coupling with barbs (530) of outer shaft (510). In other words, slots (670) may allow arms (668) to inwardly flex. As shown, proximal end (658) of body member (610) also includes a tab (676) to rotatably align with tab receiving portion (532).

4. Second Alternative Exemplary Coupling Feature

Figure 23:
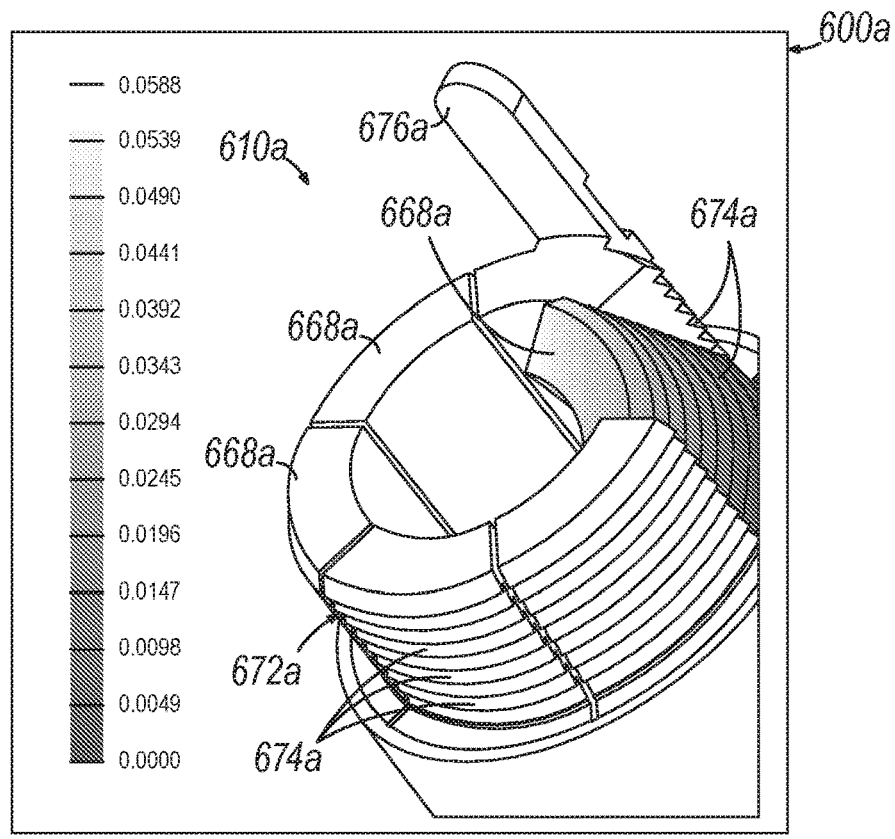
FIG. 23 depicts a chart of the deflection of an arm of a second exemplary alternative body member upon loading.
Figure 24:
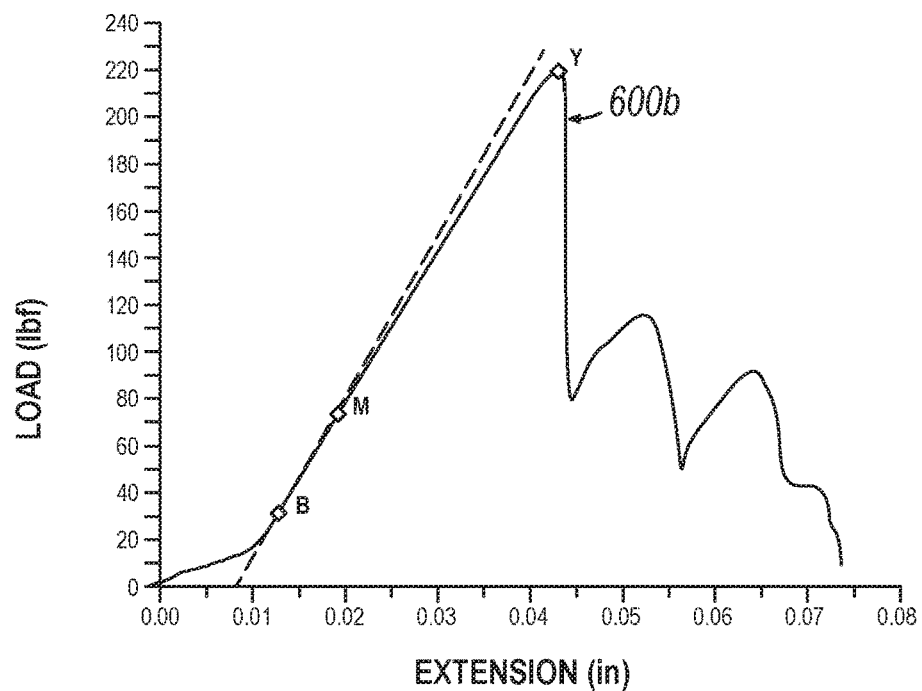
FIG. 24 depicts a graph showing a plot the load versus the extension of arm of the body member of FIG. 23.

FIGS. 23-24 show an exemplary distal end of a second exemplary alternative body member (610a). FIG. 23 depicts a graph showing an exemplary chart (600a) of radially inward deflection of a single arm (668a) of body member (600a) under an exemplary loading condition. As shown in FIG. 23, body member (610a) includes arms (668a). As shown, coupling feature (672a) is disposed on arms (668a). Coupling feature (672a) includes annular barbs (674a). Body member (610a) is similar to body member (610), and may be formed from a polymer material. For example, the polymer material of body member (610a) may have a tensile strength of approximately 120 lbs.

FIG. 24 shows a graph of a plot (600b) of load (measured in lbf) versus radial deflection (labeled as "extension") of arm (668a) of FIG. 23. As shown by plot (600b), body member (610a) may be configured to separate from an outer shaft (e.g., outer shaft (510)) upon application of an axial separation load that is greater than or equal to approximately 225 lbs. For example, the tensile strength of the polymer material of body member (610) may be approximately 38,000 psi. The tensile strength of the polymer material of body member (610a) may be approximately 52 MPa which equals approximately 7,541 psi. An exemplary tensile strength ratio of body member (610) relative to body member (610a) may be approximately 5.04 (38,000 psi/7,541 psi). The separation load to separate outer shaft (510) from body member (610) may be approximately 1134 lbs (225 lbs×5.04).

B. First Exemplary Alternative Coupling

1. Overview

Figure 25:
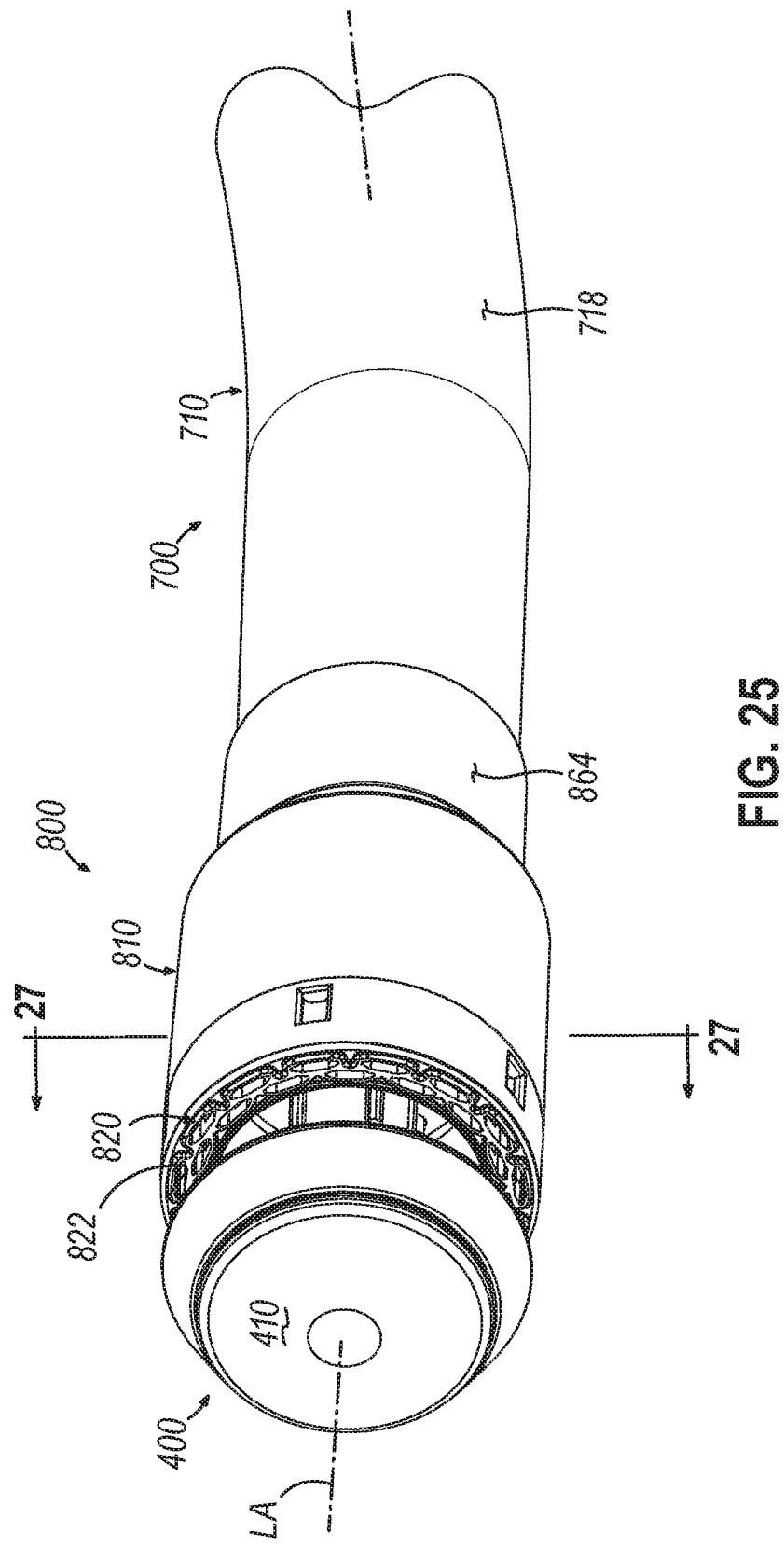
FIG. 25 depicts a perspective view of a second exemplary alternative stapling head assembly coupled with a second exemplary alternative shaft assembly that may be incorporated into the circular stapler of FIG. 1, with the stapling head assembly being coupled with the anvil of FIG. 4.
Figure 26:
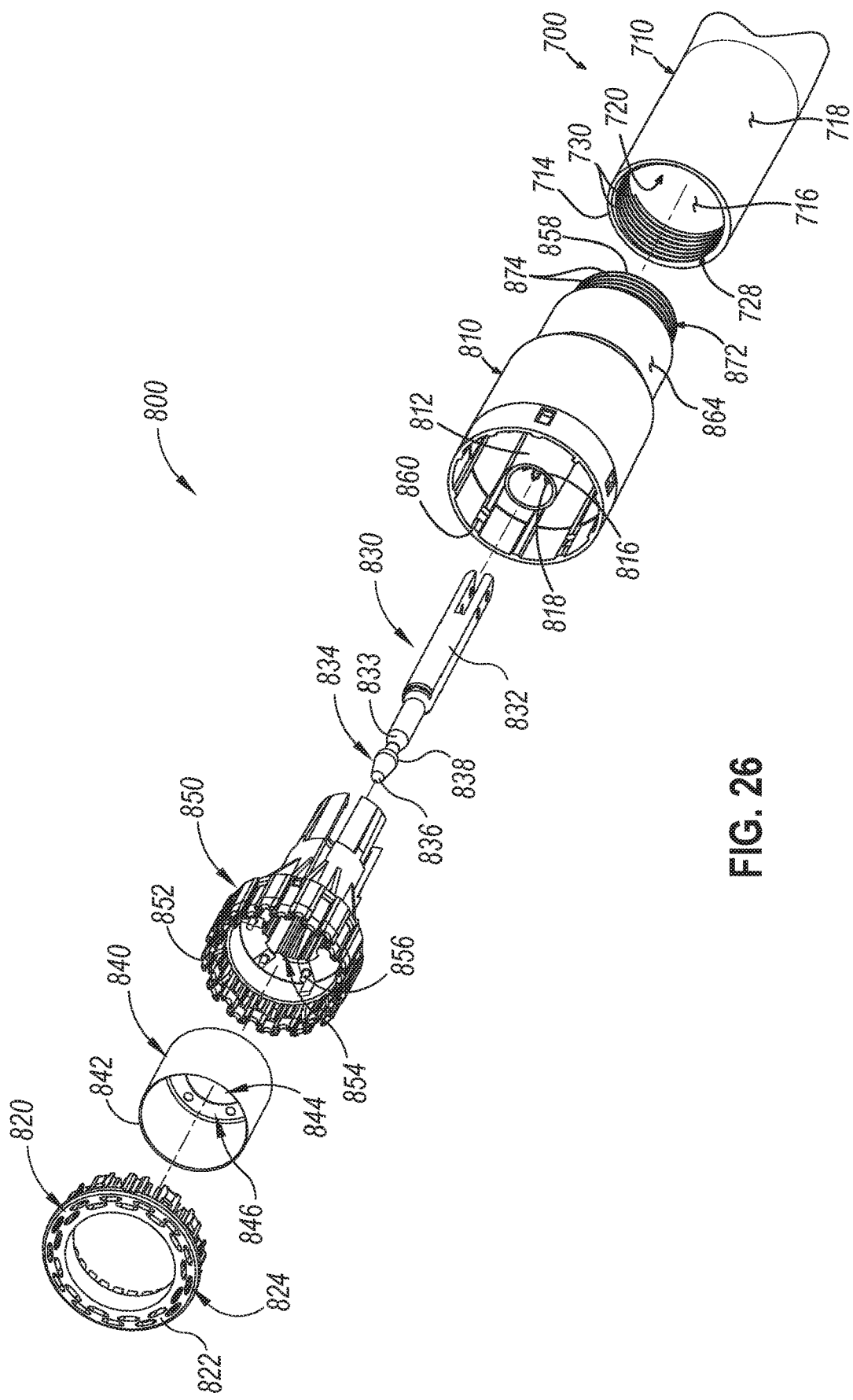
FIG. 26 depicts an exploded perspective view of a third exemplary alternative body member of the stapling head assembly and a second exemplary alternative outer shaft of the shaft assembly of FIG. 25, with the body member and the outer shaft including second exemplary coupling features.
Figure 27:
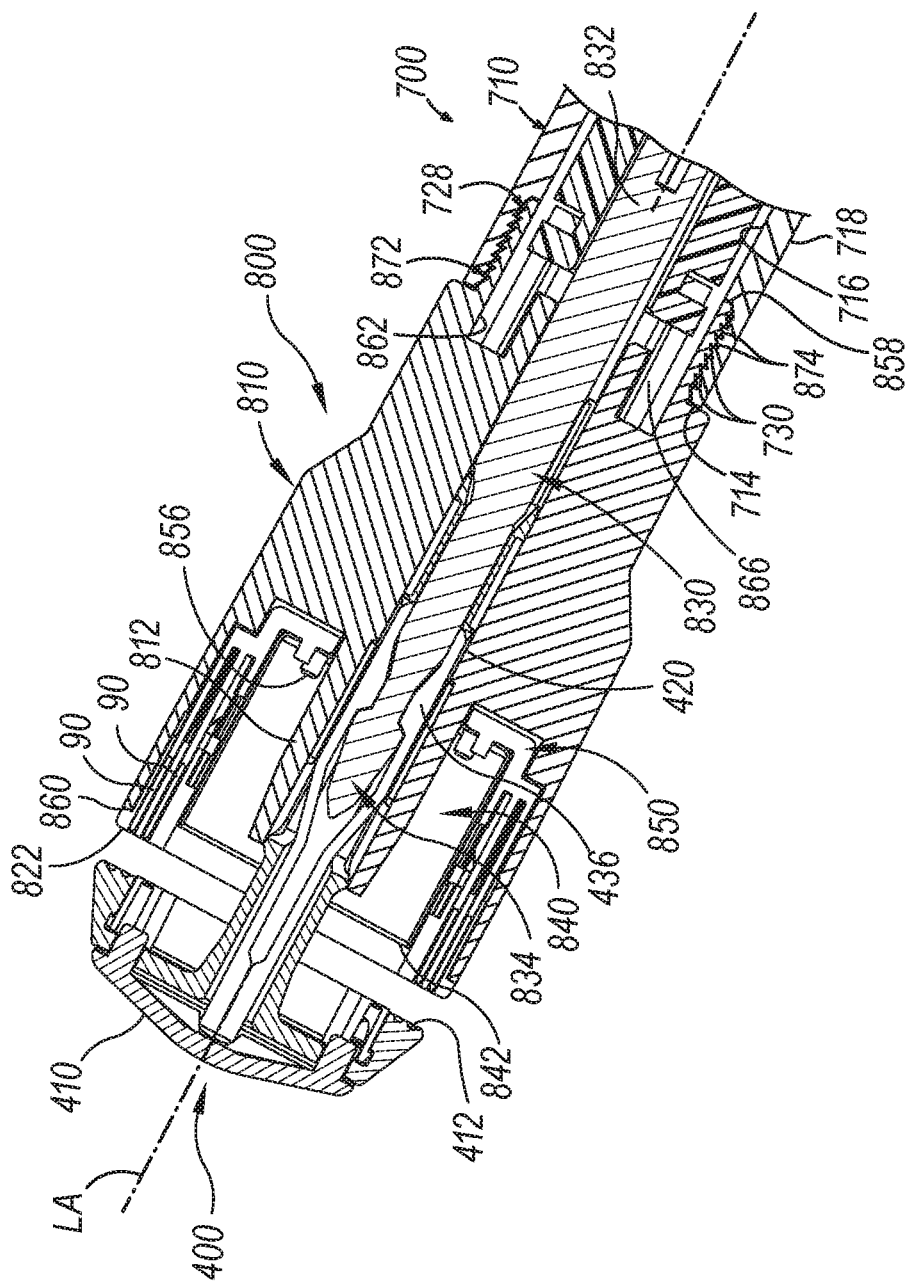
FIG. 27 depicts a cross-sectional side view of the stapling head assembly and the shaft assembly of FIG. 25 taken along line 27-27 of FIG. 25, with the body member being coupled together with the outer shaft using the coupling features of FIG. 26.

FIGS. 25-27 show a second exemplary alternative shaft assembly (700) coupled with a second exemplary alternative stapling head assembly (800). Particularly, FIG. 25 shows shaft assembly (700) coupled with stapling head assembly (800), as well as anvil (400) previously described with reference to FIGS. 4-6 coupled with stapling head assembly (800). FIG. 26 shows an exploded perspective view of a second exemplary alternative outer shaft (710) of shaft assembly (700) and a third exemplary alternative body member (810) of stapling head assembly (800) of FIG. 25. FIG. 27 shows a cross-sectional side view of stapling head assembly (800) and shaft assembly (700) of FIG. 25 taken along line 27-27 of FIG. 25, with body member (810) being coupled together with outer shaft (710) using coupling features of FIG. 26.

Similar to outer shaft (510) and body member (610), outer shaft (710) and body member (810) may be incorporated into a modified version of instrument (10), which may include a body (shown as handle assembly (100) in FIGS. 1-3), an anvil (shown as anvil (400), a shaft (shown as shaft assembly (700)), and a stapling head assembly (800). Outer shaft (710) and body member (810) of this example are configured and operable like outer shaft (210) and body member (310), with differences described below. For example, outer shaft (710) may be insertable into shaft assembly (200) in place of outer shaft (210). Similarly, body member (810) may be insertable into stapling head assembly (300) in place of body member (310).

2. First Exemplary Alternative Shaft Assembly Including First Exemplary Alternative Outer Shaft As shown in FIGS. 25-27, shaft assembly (700) extends between handle assembly (100) and stapling head assembly (800). Stapling head assembly (800) is positioned at distal end (714) of outer shaft (710). Outer shaft (710) includes proximal and distal ends (712, 714). Outer shaft (710) includes inner and outer surfaces (716, 718). Inner surface (716) defines a lumen (720). Outer shaft (710) also includes proximal and distal recessed surfaces (722, 724). Outer shaft (710) is tubular and may include a preformed bend (726).

Outer shaft (710) includes a coupling feature (728). Coupling feature (728) includes threading (730). While threading (730) are shown as being helical threading and completely around the circumference of inner surface (716), it is also envisioned that threading (730) may vary. Inner surface (716) of outer shaft (710) includes threading (730) of outer shaft (710). Outer shaft (710) also includes a tab receiving portion (732) configured to receive tab (876) to assist with rotational alignment of outer shaft (710) and body member (810). Similar to shaft assembly (200), shaft assembly (700) further includes a trocar actuation rod (similar to trocar actuation rod (220)) and a trocar actuation band assembly (similar to trocar actuation band assembly (230)) which are shown in FIG. 3.

3. First Exemplary Stapling Head Assembly Including First Exemplary Alternative Body Member As shown in FIGS. 25-27, stapling head assembly (800) may be operable to drive at least one annular array of staples (90) though tissue similar to stapling head assembly (300). As shown, stapling head assembly (800) comprises body member (810), a deck member (820), an anvil coupling feature (shown as trocar (830)), a knife member (840), a staple driver member (850), and at least one annular array of staples (90). Stapling head assembly (800) defines a longitudinal axis (LA). Stapling head assembly (800) may be coupled with anvil (400) as shown and described with reference to FIGS. 4-6.

Similar to deck member (320), deck member (820) is fixedly secured to body member (810). Deck member (820) includes a distally presented deck surface (822) defining two concentric annular arrays of staple openings (824). Staple openings (824) are arranged to correspond with the arrangement of staple drivers (852) of staple driver member (850) and staple forming pockets (414) of anvil (400). Similar to staple driver member (350, 650), staple driver member (850) is operable to drive at least one annular array of staples (80) though tissue. Similar to trocar (330, 630), trocar (830) includes latch members (430), latch shelves (436), proximal surface (838) of a head (834) of trocar (830).

Similar to knife members (340, 640), knife member (840) includes a distally presented, sharp circular cutting edge (842) configured to cut through tissue. Knife member (840) defines an opening (844) that is configured to coaxially receive inner core member (812) of body member (810). An annular array of openings (846) formed in knife member (840) is configured to complement the annular array of studs (856) of staple driver member (850), such that knife member (840) is fixedly secured to staple driver member (850) via studs (856) and openings (846).

Similar to inner core member (612), inner core member (812) of body member (810) defines a bore (814) configured to receive staple driver member (850) at least partially therein. A plurality of longitudinally extending splines (816) are equidistantly spaced in an angular array within bore (814). The distal ends of splines (816) include lead-in edges (818) that are configured to complement lead-in edges (428) of splines (426) on shank (420) of anvil (400). Body member (810) may house staple driver member (850) and knife member (840). Body member (810) includes proximal and distal ends (858, 860). Body member (810) includes inner and outer surfaces (862, 864). Inner surface (862) defines a cavity (866) that may be concentrically aligned with bore 614) along longitudinal axis (LA). Body member (810) is not shown as including arms or slots, unlike body member (610) that includes arms (668) and slots (670). Similar to outer shaft (510) and body member (610), outer shaft (510) and body member (810) may be formed from a polymer material.

Body member (810) includes at least one coupling feature (872) that is configured to mechanically couple with coupling feature (728) of outer shaft (710). Coupling feature (872) includes threading (874) formed by a plurality of individual threads that are spaced equally from one another. While threading (874) is shown as helical threading extending along the entire circumference, threading (874) vary. As shown in FIG. 27, threading (874) may be rotatably engaged with threading (730) of outer shaft (710) when suitably coupled. Threading (730, 874) may be coupled together by rotating at least one of outer shaft (710) or body member (810) relative to the other of outer shaft (710) or body member (810). Coupling feature (872) of body member (810) may form a removable connection with coupling feature (728) of outer shaft (710), such that coupling features (728, 872) allow for separation of outer shaft (710) and body member (810) once coupled. As shown, threading (874) is disposed on outer surface (864) of body member (810) to suitably couple with threading (730) disposed on inner surface (716) of outer shaft (710). Alternatively, this arrangement may be reversed, such that threading (730) may be disposed on outer surface (718) of outer shaft (710) with corresponding threading (730) of body member (810) being disposed on inner surface (862) of body member (810).

C. Exemplary Coupling Method

A method of manufacturing instrument (10) by coupling shaft assembly (500, 700) with stapling head assembly (600, 800) is also described. The method may include aligning a proximal end (658, 858) of body member (610, 810) coaxially with a distal end (514, 714) of outer shaft (510, 710). The method may also include engaging coupling feature (672, 872) disposed on a proximal end of the body member (610, 810) with coupling feature (528, 728) disposed on a distal end of outer shaft (510, 710) to couple the stapling head assembly (600, 800) with shaft assembly (500, 700) in the absence of a magnetic field.

As shown, in FIGS. 17 and 22, the coupling step may include engaging at least one barb (530) of outer shaft (510) with at least one barb (674) of body member (610) to non-releasably couple together shaft assembly (500) and stapling head assembly (600) together. Alternatively, the coupling step may include rotatably engaging threading (730) of outer shaft (710) with threading (874) of body member (810) to rotatably couple shaft assembly (700) and stapling head assembly (800) together. Coupling features (528, 672, 728, 872) (e.g., barbs (530, 674) and threading (730, 874)) may eliminate the magneforming step. Eliminating the magneforming step may eliminate the use of a magnetic field and ferule (276). Additionally, the use of discrete coupling features (528, 672, 728, 872) may allow the coupling between outer shaft (510, 710) and body member (610, 810) to be torqued to a desired a force or pushed together to a desired displacement to ensure the desired connection between outer shaft (510, 710) and body member (610, 810) has been obtained. For example, this may include reducing over torqueing or under torqueing threading (730) of outer shaft (710) and threading (874) of body member (810).

VII. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body; (b) a shaft extending distally from the body, wherein the shaft includes a coupling feature, wherein the coupling feature includes threading or at least one barb; and (c) a stapling head assembly configured to cut and staple tissue, wherein the stapling head assembly is positioned at a distal end of the shaft, wherein the stapling head assembly comprises: (i) a knife member, wherein the knife member includes a circular cutting edge configured to cut through tissue, and (ii) a body member configured to house the knife member, wherein the body member includes a coupling feature that is configured to mechanically couple with the coupling feature of the shaft, wherein the coupling feature of the body member includes threading or at least one barb.

Example 2

The apparatus of Example 1, wherein the at least one barb of the body member is configured to be translated into engagement with the at least one barb of the shaft using a push fit.

Example 3

The apparatus of any one or more of Examples 1 through 2, wherein the at least one barb of the shaft includes a plurality of ratcheting barbs, wherein the at least one barb of the body member includes a plurality of ratcheting barbs, wherein at least one of the ratcheting barbs of the shaft is lockingly engaged with at least one of the ratcheting barbs of the body member.

Example 4

The apparatus of Example 3, wherein the body member includes an outer surface, wherein the outer surface includes the ratcheting barbs of the body member, wherein the shaft includes an inner surface, wherein the inner surface includes the ratcheting barbs of the shaft.

Example 5

The apparatus of any one or more of Examples 1 through 4, wherein one of the body member or the shaft includes at least one arm that is configured to radially deflect upon coupling with the other of the body member or the shaft.

Example 6

The apparatus of any one or more of Examples 1, 2, and 5, wherein the body member includes a plurality of arms, wherein the at least one barb of the body member is circumferentially disposed on each of the arms, wherein the at least one barb of the shaft includes a plurality of barbs that are lockingly engaged with the at least one barb formed on the arms.

Example 7

The apparatus of Example 1, wherein the threading of the body member is configured to be rotated into engagement with the threading of the shaft.

Example 8

The apparatus of any one or more of Examples 1 and 7, wherein the threading of the shaft includes helical threading, wherein the threading of the body member includes helical threading that is lockingly engaged with the helical threading of the shaft.

Example 9

The apparatus of any one or more of Examples 1, 7, and 8, wherein the body member includes an outer surface, wherein the outer surface includes the helical threading of the body member, wherein the shaft includes an inner surface, wherein the inner surface includes the helical threading of the shaft.

Example 10

The apparatus of any one or more of Examples 1 through 6, wherein one of the shaft or the body member includes a tab, wherein the other of the shaft or the body member includes a receiving portion that receives the tab to ensure the coupling features of the shaft and the body member and rotatably aligned.

Example 11

The apparatus of any one or more of Examples 1 through 10, wherein the body member includes an inner core member that defines a bore configured to receive an anvil coupling feature therethrough.

Example 12

The apparatus of any one or more of Examples 1 through 11, further comprising an anvil that includes a plurality of splines, wherein the body member includes a plurality of splines are configured to engage the splines of the anvil to provide a predetermined angular alignment between the anvil and the stapling head assembly.

Example 13

The apparatus of any one or more of Examples 1 through 12, wherein the stapling head assembly includes a staple driver member and at least one annular array of staples, wherein the staple driver member is operable to drive the at least one annular array of staples though the tissue.

Example 14

The apparatus of Example 13, wherein the body member includes a cavity configured to receive the staple driver member at least partially therein.

Example 15

The apparatus of any one or more of Examples 13 and 14, wherein the stapling head assembly includes an anvil coupling feature, wherein the apparatus further comprises an anvil, wherein the anvil is configured to couple with the anvil coupling feature, wherein the anvil is further configured to deform the at least one annular array of staples driven by the staple driver member.

Example 16

An apparatus comprising: (a) a body; (b) a shaft extending distally from the body, wherein the shaft includes a distal end, wherein the distal end includes helical threading or at least one barb; and (c) a stapling head assembly positioned at a distal end of the shaft, wherein the stapling head assembly comprises: (i) at least one annular array of staples, (ii) a staple driver member operable to drive the at least one annular array of staples though tissue, (iii) a knife member configured to cut through the tissue, and (iv) a body member configured to house the staple driver member and the knife member, wherein the body member includes helical threading or at least one barb that is configured to couple with the helical threading or the at least one barb of the distal end of the shaft.

Example 17

The apparatus of Example 16, wherein the stapling head assembly includes an anvil coupling feature, wherein the apparatus further comprises an anvil, wherein the anvil is configured to couple with the anvil coupling feature, wherein the anvil is further configured to deform the at least one annular array of staples driven by the staple driver member.

Example 18

A method of manufacturing an apparatus, wherein the apparatus includes a body, a shaft extending distally from the body, and a stapling head assembly positioned at a distal end of the shaft, wherein the stapling head assembly includes a body member and a knife member, wherein the knife member includes a circular cutting edge that is configured to cut through tissue, the method comprising: (a) aligning a proximal end of the body member coaxially with a distal end of the shaft; and (b) engaging a first coupling feature disposed on a proximal end of the body member with a second coupling feature disposed on a distal end of the shaft to non-releasably couple the stapling head assembly with the shaft in the absence of a magnetic field.

Example 19

The method of Example 18, wherein the first coupling feature includes at least one ratcheting barb, wherein the second coupling feature includes at least one ratcheting barb, wherein the engaging step further comprises engaging the at least one ratcheting barb of the body member with the at least one ratcheting barb of the shaft to couple the shaft and the stapling head assembly together.

Example 20

The method of Example 18, wherein the first coupling feature includes helical threading, wherein the second coupling feature includes helical threading, wherein the coupling step further comprises engaging the helical threading of the body member with the helical threading of the shaft to couple the shaft and the stapling head assembly together.

XIII. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may also be readily combined with one or more teachings of U.S. Pub. No. 2017/0258471, entitled "Methods and Systems for Performing Circular Stapling," published Sep. 14, 2017, issued as U.S. Pat. No. 10,709,452 on Jul. 14, 2020, the disclosure of which is incorporated by reference herein; U.S. Pub. No. 2015/0083772, entitled "Surgical Stapler with Rotary Cam Drive and Return," published Mar. 26, 2015, now abandoned, the disclosure of which is incorporated by reference herein; U.S. Pat. No. 9,936,949, entitled "Surgical Stapling Instrument with Drive Assembly Having Toggle Features," issued Apr. 10, 2018, the disclosure of which is incorporated by reference herein; U.S. Pat. No. 9,907,552, entitled "Control Features for Motorized Surgical Stapling Instrument," issued Mar. 6, 2018, the disclosure of which is incorporated by reference herein; U.S. Pat. No. 9,713,469, entitled "Surgical Stapler with Rotary Cam Drive," issued Jul. 25, 2017, the disclosure of which is incorporated by reference herein; U.S. Pat. No. 10,226,253, entitled "Firing Assembly for Circular Stapler," issued Mar. 12, 2019, the disclosure of which is incorporated by reference herein; U.S. Pub. No. U.S. Pat. No. 10,478,189, entitled "Method of Applying an Annular Array of Staples to Tissue," issued Nov. 19, 2019, the disclosure of which is incorporated by reference herein. Various suitable ways in which the teachings herein may be combined with the teachings of the above-referenced patents, publications, and patent applications will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). As another merely illustrative example, the various teachings herein may be readily applied to a motorized electrosurgical device. For instance, various teachings herein may be readily combined with various teachings of U.S. Pat. No. 9,161,803, entitled "Motor Driven Electrosurgical Device with Mechanical and Electrical Feedback," issued Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a body;
   (b) a shaft extending distally from the body, wherein the shaft includes a coupling feature, wherein the coupling feature includes at least one barb;
   (c) an anvil; and
   (d) a stapling head assembly configured to cut and staple tissue, wherein the stapling head assembly is positioned at a distal end of the shaft, wherein the stapling head assembly comprises:
      (i) a knife member, wherein the knife member includes a circular cutting edge configured to cut through tissue,
      (ii) a staple driver member configured to drive at least one annular array of staples distally towards the anvil, and
      (iii) a body member configured to house the knife member, wherein the body member includes a coupling feature that is configured to mechanically couple with the coupling feature of the shaft, wherein the coupling feature of the body member includes at least one barb.

2. The apparatus of claim 1, wherein the at least one barb of the body member is configured to be translated into engagement with the at least one barb of the shaft using a push fit.

3. The apparatus of claim 1, wherein the at least one barb of the shaft includes a plurality of ratcheting barbs, wherein the at least one barb of the body member includes a plurality of ratcheting barbs, wherein at least one of the ratcheting barbs of the shaft is lockingly engaged with at least one of the ratcheting barbs of the body member.

4. The apparatus of claim 3, wherein the body member includes an outer surface, wherein the outer surface includes the ratcheting barbs of the body member, wherein the shaft includes an inner surface, wherein the inner surface includes the ratcheting barbs of the shaft.

5. The apparatus of claim 1, wherein one of the body member or the shaft includes at least one arm that is configured to radially deflect upon coupling with the other of the body member or the shaft.

6. The apparatus of claim 1, wherein the body member includes a plurality of arms, wherein the at least one barb of the body member is circumferentially disposed on each of the arms, wherein the at least one barb of the shaft includes a plurality of barbs that are lockingly engaged with the at least one barb formed on the arms.

7. The apparatus of claim 1, wherein one of the shaft or the body member includes a tab, wherein the other of the shaft or the body member includes a receiving portion that receives the tab to ensure the coupling features of the shaft and the body member and rotatably aligned.

8. The apparatus of claim 1, wherein the body member includes an inner core member that defines a bore configured to receive an anvil coupling feature therethrough to couple with the anvil.

9. The apparatus of claim 1, wherein the anvil includes a plurality of splines, wherein the body member includes a plurality of splines are configured to engage the splines of the anvil to provide a predetermined angular alignment between the anvil and the stapling head assembly.

10. The apparatus of claim 1, wherein the stapling head assembly includes the at least one annular array of staples, wherein the staple driver member is operable to drive the at least one annular array of staples though the tissue.

11. The apparatus of claim 10, wherein the stapling head assembly includes an anvil coupling feature, wherein the anvil is configured to couple with the anvil coupling feature, wherein the anvil is further configured to deform the at least one annular array of staples driven by the staple driver member.

12. The apparatus of claim 1, wherein the body member includes a cavity configured to receive the staple driver member at least partially therein.

13. A method of manufacturing an apparatus, wherein the apparatus includes a body, a shaft extending distally from the body, and a stapling head assembly positioned at a distal end of the shaft, wherein the stapling head assembly includes a body member and a knife member, wherein the knife member includes a circular cutting edge that is configured to cut through tissue, the method comprising:
   (a) aligning a proximal end of the body member coaxially with a distal end of the shaft; and
   (b) engaging at least one barb disposed on a proximal end of the body member with at least one barb disposed on a distal end of the shaft to non-releasably couple the stapling head assembly with the shaft.

14. The method of claim 13, wherein the stapling head assembly includes a staple driver member and at least one annular array of staples, the method further comprising driving at least one annular array of staples away from the proximal end of the body member using the staple driver member.

15. An apparatus comprising:
(a) a body;
(b) a shaft extending distally from the body, wherein the shaft includes a coupling feature, wherein the coupling feature includes threading or at least one barb; and
(c) a stapling head assembly configured to cut and staple tissue, wherein the stapling head assembly is positioned at a distal end of the shaft, wherein the stapling head assembly comprises:
  (i) a knife member, wherein the knife member includes a circular cutting edge configured to cut through tissue, and
  (ii) a body member configured to house the knife member, wherein the body member includes a coupling feature that is configured to mechanically couple with the coupling feature of the shaft, wherein the coupling feature of the body member includes threading or at least one barb, wherein one of the body member or the shaft includes at least one arm configured to radially deflect upon coupling of the body member with the shaft.

16. The apparatus of claim 15, wherein the threading of the shaft includes helical threading, wherein the threading of the body member includes helical threading that is lockingly engaged with the helical threading of the shaft.

17. The apparatus of claim 16, wherein the body member includes an outer surface, wherein the outer surface includes the helical threading of the body member, wherein the shaft includes an inner surface, wherein the inner surface includes the helical threading of the shaft.

18. The method of claim 14, wherein the stapling head assembly includes an anvil coupling feature and at least one annular array of staples, wherein the apparatus further comprises an anvil, the method further comprising:
(a) coupling the anvil with the anvil coupling feature; and
(b) deforming the at least one annular array of staples driven by the staple driver member using the anvil.

19. The apparatus of claim 15, wherein the coupling feature of the body member includes the threading, wherein the coupling feature of the shaft includes the threading, wherein the threading of the body member is configured to be rotated into engagement with the threading of the shaft.

20. The apparatus of claim 15, wherein the coupling feature of the shaft includes the at least one barb, wherein the coupling feature of the body member includes the at least one barb configured to be translated into engagement with the at least one barb of the shaft using a push fit.

* * * * *